(12) United States Patent
Mauch et al.

(10) Patent No.: US 11,786,370 B2
(45) Date of Patent: Oct. 17, 2023

(54) DELIVERY SYSTEMS FOR DELIVERING PROSTHETIC HEART VALVE DEVICES AND ASSOCIATED METHODS

(71) Applicant: Twelve, Inc., Redwood City, CA (US)

(72) Inventors: Kevin Mauch, Windsor, CA (US); Joshua Dwork, Santa Rosa, CA (US); Finn Rinne, Santa Rosa, CA (US); Siyan Som, Fulton, CA (US); Estella Wong, Santa Rosa, CA (US)

(73) Assignee: Twelve, Inc., Redwood City, CA (US)

( * ) Notice: Subject to any disclaimer, the term of this patent is extended or adjusted under 35 U.S.C. 154(b) by 314 days.

(21) Appl. No.: 17/063,216

(22) Filed: Oct. 5, 2020

(65) Prior Publication Data

US 2021/0085450 A1   Mar. 25, 2021

Related U.S. Application Data

(63) Continuation of application No. 15/592,507, filed on May 11, 2017, now Pat. No. 10,792,151.

(51) Int. Cl.
*A61F 2/24* (2006.01)

(52) U.S. Cl.
CPC .......... *A61F 2/243* (2013.01); *A61F 2/2409* (2013.01); *A61F 2/2418* (2013.01);
(Continued)

(58) Field of Classification Search
CPC .... A61F 2/2409; A61F 2/2418; A61F 2/2436; A61F 2210/014; A61F 2230/0054
See application file for complete search history.

(56) References Cited

U.S. PATENT DOCUMENTS

| 3,526,219 A | 9/1970 | Balamuth |
| 3,565,062 A | 2/1971 | Kuris |

(Continued)

FOREIGN PATENT DOCUMENTS

| CN | 1440261 A | 9/2003 |
| CN | 101076290 A | 11/2007 |

(Continued)

OTHER PUBLICATIONS

US 9,265,606 B2, 02/2016, Buchbinder et al. (withdrawn)
(Continued)

*Primary Examiner* — Alexander J Orkin
(74) *Attorney, Agent, or Firm* — Medler Ferro Woodhouse & Mills PLLC

(57) ABSTRACT

Systems for delivering prosthetic heart valve devices can include, for example, an elongated catheter body, a deliver capsule carried by the catheter body, and an expandable atraumatic member. The delivery capsule includes a platform and a housing having an outer wall and a proximal rim, and the platform is configured to be releasably coupled to a prosthetic heart valve device. The housing is configured to slide along the platform from a containment configuration to a deployment configuration. The expandable atraumatic member has an atraumatic surface and a peripheral portion. The atraumatic member has a compacted configuration and an expanded configuration in which the peripheral portion extends laterally outward over the proximal rim of the housing to protect tissue of the heart and the vasculature from potentially being damaged by the proximal rim of the housing as the delivery system is withdrawn in a proximal direction through the patient.

19 Claims, 18 Drawing Sheets

(52) U.S. Cl.
CPC .... *A61F 2/2436* (2013.01); *A61F 2210/0014* (2013.01); *A61F 2220/005* (2013.01); *A61F 2220/0016* (2013.01); *A61F 2220/0058* (2013.01); *A61F 2220/0075* (2013.01); *A61F 2230/0054* (2013.01); *A61F 2250/0069* (2013.01)

(56) References Cited

U.S. PATENT DOCUMENTS

| | | |
|---|---|---|
| 3,589,363 A | 6/1971 | Banko et al. |
| 3,667,474 A | 6/1972 | Lapkin et al. |
| 3,823,717 A | 7/1974 | Pohlman et al. |
| 3,861,391 A | 1/1975 | Antonevich et al. |
| 3,896,811 A | 7/1975 | Storz |
| 4,042,979 A | 8/1977 | Angell |
| 4,188,952 A | 2/1980 | Loschilov et al. |
| 4,431,006 A | 2/1984 | Trimmer et al. |
| 4,445,509 A | 5/1984 | Auth |
| 4,484,579 A | 11/1984 | Meno et al. |
| 4,490,859 A | 1/1985 | Black et al. |
| 4,587,958 A | 5/1986 | Noguchi et al. |
| 4,589,419 A | 5/1986 | Laughlin et al. |
| 4,602,911 A | 7/1986 | Ahmadi et al. |
| 4,646,736 A | 3/1987 | Auth |
| 4,692,139 A | 9/1987 | Stiles |
| 4,747,821 A | 5/1988 | Kensey et al. |
| 4,750,902 A | 6/1988 | Wuchinich et al. |
| 4,777,951 A | 10/1988 | Cribier et al. |
| 4,787,388 A | 11/1988 | Hofmann |
| 4,796,629 A | 1/1989 | Grayzel |
| 4,808,153 A | 2/1989 | Parisi |
| 4,819,751 A | 4/1989 | Shimada et al. |
| 4,841,977 A | 6/1989 | Griffith et al. |
| 4,870,953 A | 10/1989 | DonMicheal et al. |
| 4,878,495 A | 11/1989 | Grayzel |
| 4,898,575 A | 2/1990 | Fischell et al. |
| 4,909,252 A | 3/1990 | Goldberger |
| 4,919,133 A | 4/1990 | Chiang |
| 4,920,954 A | 5/1990 | Alliger et al. |
| 4,936,281 A | 6/1990 | Stasz |
| 4,960,411 A | 10/1990 | Buchbinder |
| 4,986,830 A | 1/1991 | Owens et al. |
| 4,990,134 A | 2/1991 | Auth |
| 5,058,570 A | 10/1991 | Idemoto et al. |
| 5,069,664 A | 12/1991 | Guess et al. |
| 5,076,276 A | 12/1991 | Sakurai et al. |
| 5,106,302 A | 4/1992 | Farzin-Nia et al. |
| 5,248,296 A | 9/1993 | Alliger |
| 5,267,954 A | 12/1993 | Nita |
| 5,269,291 A | 12/1993 | Carter |
| 5,295,958 A | 3/1994 | Shturman |
| 5,304,115 A | 4/1994 | Pflueger et al. |
| 5,314,407 A | 5/1994 | Auth et al. |
| 5,318,014 A | 6/1994 | Carter |
| 5,332,402 A | 7/1994 | Teitelbaum |
| 5,344,426 A | 9/1994 | Lau et al. |
| 5,352,199 A | 10/1994 | Tower |
| 5,356,418 A | 10/1994 | Shturman |
| 5,397,293 A | 3/1995 | Alliger et al. |
| 5,411,552 A | 5/1995 | Andersen et al. |
| 5,443,446 A | 8/1995 | Shturman |
| 5,449,373 A | 9/1995 | Pinchasik et al. |
| 5,489,297 A | 2/1996 | Duran |
| 5,584,879 A | 12/1996 | Reimold et al. |
| 5,609,151 A | 3/1997 | Mulier et al. |
| 5,626,603 A | 5/1997 | Venturelli et al. |
| 5,656,036 A | 8/1997 | Palmaz |
| 5,662,671 A | 9/1997 | Barbut et al. |
| 5,681,336 A | 10/1997 | Clement et al. |
| 5,695,507 A | 12/1997 | Auth et al. |
| 5,725,494 A | 3/1998 | Brisken |
| 5,782,931 A | 7/1998 | Yang et al. |
| 5,817,101 A | 10/1998 | Fiedler |
| 5,827,229 A | 10/1998 | Auth et al. |
| 5,827,321 A | 10/1998 | Roubin et al. |
| 5,840,081 A | 11/1998 | Andersen et al. |
| 5,853,422 A | 12/1998 | Huebsch et al. |
| 5,855,601 A | 1/1999 | Bessler et al. |
| 5,868,781 A | 2/1999 | Killion |
| 5,873,811 A | 2/1999 | Wang et al. |
| 5,904,679 A | 5/1999 | Clayman |
| 5,957,882 A | 9/1999 | Nita et al. |
| 5,972,004 A | 10/1999 | Williamson, IV et al. |
| 5,989,208 A | 11/1999 | Nita |
| 5,989,280 A | 11/1999 | Euteneuer et al. |
| 6,047,700 A | 4/2000 | Eggers et al. |
| 6,056,759 A | 5/2000 | Fiedler |
| 6,085,754 A | 7/2000 | Alferness et al. |
| 6,113,608 A | 9/2000 | Monroe et al. |
| RE36,939 E | 10/2000 | Tachibana et al. |
| 6,129,734 A | 10/2000 | Shturman et al. |
| 6,132,444 A | 10/2000 | Shturman et al. |
| 6,168,579 B1 | 1/2001 | Tsugita |
| 6,217,595 B1 | 4/2001 | Shturman et al. |
| 6,254,635 B1 | 7/2001 | Schroeder et al. |
| 6,295,712 B1 | 10/2001 | Shturman et al. |
| 6,306,414 B1 | 10/2001 | Koike |
| 6,321,109 B2 | 11/2001 | Ben-Haim et al. |
| 6,402,679 B1 | 6/2002 | Mortier et al. |
| 6,423,032 B2 | 7/2002 | Parodi |
| 6,425,916 B1 | 7/2002 | Garrison et al. |
| 6,440,164 B1 | 8/2002 | DiMatteo et al. |
| 6,454,737 B1 | 9/2002 | Nita et al. |
| 6,454,757 B1 | 9/2002 | Nita et al. |
| 6,454,799 B1 | 9/2002 | Schreck |
| 6,458,153 B1 | 10/2002 | Bailey et al. |
| 6,461,382 B1 | 10/2002 | Cao |
| 6,494,890 B1 | 12/2002 | Shturman et al. |
| 6,494,891 B1 | 12/2002 | Cornish et al. |
| 6,505,080 B1 | 1/2003 | Sutton |
| 6,530,952 B2 | 3/2003 | Vesely |
| 6,540,782 B1 | 4/2003 | Snyders |
| 6,562,067 B2 | 5/2003 | Mathis |
| 6,565,588 B1 | 5/2003 | Clement et al. |
| 6,569,196 B1 | 5/2003 | Vesely |
| 6,579,308 B1 | 6/2003 | Jansen et al. |
| 6,582,462 B1 | 6/2003 | Andersen et al. |
| 6,595,912 B2 | 7/2003 | Lau et al. |
| 6,605,109 B2 | 8/2003 | Fiedler |
| 6,616,689 B1 | 9/2003 | Ainsworth et al. |
| 6,623,452 B2 | 9/2003 | Chien et al. |
| 6,638,288 B1 | 10/2003 | Shturman et al. |
| 6,648,854 B1 | 11/2003 | Patterson et al. |
| 6,689,086 B1 | 2/2004 | Nita et al. |
| 6,702,748 B1 | 3/2004 | Nita et al. |
| 6,730,121 B2 | 5/2004 | Ortiz et al. |
| 6,746,463 B1 | 6/2004 | Schwartz |
| 6,811,801 B2 | 11/2004 | Nguyen et al. |
| 6,818,001 B2 | 11/2004 | Wulfman et al. |
| 6,843,797 B2 | 1/2005 | Nash et al. |
| 6,852,118 B2 | 2/2005 | Shturman et al. |
| 6,855,123 B2 | 2/2005 | Nita |
| 6,869,439 B2 | 3/2005 | White et al. |
| 6,951,571 B1 | 10/2005 | Srivastava |
| 6,986,775 B2 | 1/2006 | Morales et al. |
| 7,018,404 B2 | 3/2006 | Holmberg et al. |
| 7,052,487 B2 | 5/2006 | Cohn et al. |
| 7,077,861 B2 | 7/2006 | Spence |
| 7,125,420 B2 | 10/2006 | Rourke et al. |
| 7,186,264 B2 | 3/2007 | Liddicoat et al. |
| 7,261,732 B2 | 8/2007 | Justino |
| 7,296,577 B2 | 11/2007 | Lashinski et al. |
| 7,381,218 B2 | 6/2008 | Schreck |
| 7,404,824 B1 | 7/2008 | Webler et al. |
| 7,442,204 B2 | 10/2008 | Schwammenthal et al. |
| 7,473,275 B2 | 1/2009 | Marquez |
| 7,510,575 B2 | 3/2009 | Spenser et al. |
| 7,585,321 B2 | 9/2009 | Cribier |
| 7,588,582 B2 | 9/2009 | Starksen et al. |
| 7,621,948 B2 | 11/2009 | Herrmann et al. |
| 7,708,775 B2 | 5/2010 | Rowe et al. |
| 7,748,389 B2 | 7/2010 | Salahieh et al. |
| 7,753,922 B2 | 7/2010 | Starksen |
| 7,753,949 B2 | 7/2010 | Lamphere et al. |

(56) References Cited

U.S. PATENT DOCUMENTS

| | | |
|---|---|---|
| 7,803,168 B2 | 9/2010 | Gifford et al. |
| 7,857,845 B2 | 12/2010 | Stacchino et al. |
| 7,896,915 B2 | 3/2011 | Guyenot et al. |
| 7,914,569 B2 | 3/2011 | Nguyen et al. |
| 7,942,928 B2 | 5/2011 | Webler et al. |
| 8,002,826 B2 | 8/2011 | Seguin |
| 8,016,877 B2 | 9/2011 | Seguin et al. |
| 8,052,750 B2 | 11/2011 | Tuval et al. |
| 8,062,355 B2 | 11/2011 | Figulla et al. |
| 8,109,996 B2 | 2/2012 | Stacchino et al. |
| 8,114,154 B2 | 2/2012 | Righini et al. |
| 8,252,051 B2 | 8/2012 | Chau et al. |
| 8,398,704 B2 | 3/2013 | Straubinger et al. |
| 8,403,981 B2 | 3/2013 | Forster et al. |
| 8,403,983 B2 | 3/2013 | Quadri et al. |
| 8,414,643 B2 | 4/2013 | Tuval et al. |
| 8,449,599 B2 | 5/2013 | Chau et al. |
| 8,496,671 B1 | 7/2013 | Hausen |
| 8,512,252 B2 | 8/2013 | Ludomirsky et al. |
| 8,518,107 B2 | 8/2013 | Tsukashima et al. |
| 8,523,883 B2 | 9/2013 | Saadat |
| 8,532,352 B2 | 9/2013 | Ionasec et al. |
| 8,540,767 B2 | 9/2013 | Zhang |
| 8,545,551 B2 | 10/2013 | Loulmet |
| 8,551,161 B2 | 10/2013 | Dolan |
| 8,579,788 B2 | 11/2013 | Orejola |
| 8,579,964 B2 | 11/2013 | Lane et al. |
| 8,585,755 B2 | 11/2013 | Chau et al. |
| 8,597,347 B2 | 12/2013 | Maurer et al. |
| 8,597,348 B2 | 12/2013 | Rowe et al. |
| 8,608,796 B2 | 12/2013 | Matheny |
| 8,608,797 B2 | 12/2013 | Gross et al. |
| 8,623,077 B2 | 1/2014 | Cohn |
| 8,628,566 B2 | 1/2014 | Eberhardt et al. |
| 8,632,585 B2 | 1/2014 | Seguin et al. |
| 8,632,586 B2 | 1/2014 | Spenser et al. |
| 8,634,935 B2 | 1/2014 | Gaudiani |
| 8,647,254 B2 | 2/2014 | Callas et al. |
| 8,652,203 B2 | 2/2014 | Quadri et al. |
| 8,652,204 B2 | 2/2014 | Quill et al. |
| 8,657,872 B2 | 2/2014 | Seguin |
| 8,672,998 B2 | 3/2014 | Lichtenstein et al. |
| 8,673,001 B2 | 3/2014 | Cartledge et al. |
| 8,679,176 B2 | 3/2014 | Matheny |
| 8,685,086 B2 | 4/2014 | Navia et al. |
| 8,688,234 B2 | 4/2014 | Zhu et al. |
| 8,690,858 B2 | 4/2014 | Machold et al. |
| 8,709,074 B2 | 4/2014 | Solem et al. |
| 8,712,133 B2 | 4/2014 | Guhring et al. |
| 8,715,160 B2 | 5/2014 | Raman et al. |
| 8,721,665 B2 | 5/2014 | Oz et al. |
| 8,721,718 B2 | 5/2014 | Kassab |
| 8,740,918 B2 | 6/2014 | Seguin |
| 8,747,460 B2 | 6/2014 | Tuval et al. |
| 8,758,431 B2 | 6/2014 | Orlov et al. |
| 8,758,432 B2 | 6/2014 | Solem |
| 8,771,292 B2 | 7/2014 | Allen et al. |
| 8,771,345 B2 | 7/2014 | Tuval et al. |
| 8,771,346 B2 | 7/2014 | Tuval et al. |
| 8,777,991 B2 | 7/2014 | Zarbatany et al. |
| 8,778,016 B2 | 7/2014 | Janovsky et al. |
| 8,781,580 B2 | 7/2014 | Hedberg et al. |
| 8,784,482 B2 | 7/2014 | Rahdert et al. |
| 8,792,699 B2 | 7/2014 | Guetter et al. |
| 8,795,356 B2 | 8/2014 | Quadri et al. |
| 8,801,779 B2 | 8/2014 | Seguin et al. |
| 8,808,356 B2 | 8/2014 | Braido et al. |
| 8,808,366 B2 | 8/2014 | Braido et al. |
| 8,812,431 B2 | 8/2014 | Voigt et al. |
| 8,828,043 B2 | 9/2014 | Chambers |
| 8,845,717 B2 | 9/2014 | Khairkhahan et al. |
| 8,845,723 B2 | 9/2014 | Spence et al. |
| 8,852,213 B2 | 10/2014 | Gammie et al. |
| 8,852,272 B2 | 10/2014 | Gross et al. |
| 8,858,622 B2 | 10/2014 | Machold et al. |
| 8,859,724 B2 | 10/2014 | Meier et al. |
| 8,864,822 B2 | 10/2014 | Spence et al. |
| 8,870,936 B2 | 10/2014 | Rowe |
| 8,870,948 B1 | 10/2014 | Erzberger et al. |
| 8,870,949 B2 | 10/2014 | Rowe |
| 8,894,702 B2 | 11/2014 | Quadri et al. |
| 8,900,295 B2 | 12/2014 | Migliazza et al. |
| 8,926,694 B2 | 1/2015 | Costello |
| 8,932,348 B2 | 1/2015 | Solem et al. |
| 8,951,285 B2 | 2/2015 | Sugimoto et al. |
| 8,961,597 B2 | 2/2015 | Subramanian et al. |
| 8,968,393 B2 | 3/2015 | Rothstein |
| 8,968,395 B2 | 3/2015 | Hauser et al. |
| 8,974,445 B2 | 3/2015 | Warnking et al. |
| 8,979,922 B2 | 3/2015 | Jayasinghe et al. |
| 8,979,923 B2 | 3/2015 | Spence et al. |
| 8,986,370 B2 | 3/2015 | Annest |
| 8,986,376 B2 | 3/2015 | Solem |
| 8,992,604 B2 | 3/2015 | Gross et al. |
| 9,011,522 B2 | 4/2015 | Annest |
| 9,011,523 B2 | 4/2015 | Seguin |
| 9,017,399 B2 | 4/2015 | Gross et al. |
| 9,023,098 B2 | 5/2015 | Kuehn |
| 9,023,100 B2 | 5/2015 | Quadri et al. |
| 9,050,188 B2 | 6/2015 | Schweich, Jr. et al. |
| 9,066,800 B2 | 6/2015 | Clague et al. |
| 9,084,676 B2 | 7/2015 | Chau et al. |
| 9,095,433 B2 | 8/2015 | Lutter et al. |
| 9,119,713 B2 | 9/2015 | Board et al. |
| 9,132,009 B2 | 9/2015 | Hacohen et al. |
| 9,138,312 B2 | 9/2015 | Tuval et al. |
| 9,138,313 B2 | 9/2015 | McGuckin, Jr. et al. |
| 9,180,005 B1 | 11/2015 | Lashinski et al. |
| 9,192,466 B2 | 11/2015 | Kovalsky et al. |
| 9,192,471 B2 | 11/2015 | Bolling |
| 9,232,942 B2 | 1/2016 | Seguin et al. |
| 9,232,999 B2 | 1/2016 | Maurer et al. |
| 9,241,790 B2 | 1/2016 | Lane et al. |
| 9,248,014 B2 | 2/2016 | Lane et al. |
| 9,254,192 B2 | 2/2016 | Lutter et al. |
| 9,271,833 B2 | 3/2016 | Kim et al. |
| 9,289,291 B2 | 3/2016 | Gorman, III et al. |
| 9,289,297 B2 | 3/2016 | Wilson et al. |
| 9,295,547 B2 | 3/2016 | Costello et al. |
| 9,301,836 B2 | 4/2016 | Buchbinder et al. |
| 9,308,087 B2 | 4/2016 | Lane et al. |
| 9,326,850 B2 | 5/2016 | Venkatasubramanian |
| 9,339,378 B2 | 5/2016 | Quadri et al. |
| 9,339,379 B2 | 5/2016 | Quadri et al. |
| 9,339,380 B2 | 5/2016 | Quadri et al. |
| 9,339,382 B2 | 5/2016 | Tabor et al. |
| 9,358,108 B2 | 6/2016 | Bortlein et al. |
| 9,387,075 B2 | 7/2016 | Bortlein et al. |
| 9,387,078 B2 | 7/2016 | Gross et al. |
| 9,393,111 B2 | 7/2016 | Ma et al. |
| 9,629,719 B2 | 4/2017 | Rothstein et al. |
| 9,675,454 B2 | 6/2017 | Vidlund et al. |
| 9,681,951 B2 | 6/2017 | Ratz et al. |
| 9,687,342 B2 | 6/2017 | Figulla et al. |
| 9,687,343 B2 | 6/2017 | Bortlein et al. |
| 9,693,859 B2 | 7/2017 | Braido et al. |
| 9,693,862 B2 | 7/2017 | Campbell et al. |
| 9,694,121 B2 | 7/2017 | Alexander et al. |
| 9,700,409 B2 | 7/2017 | Braido et al. |
| 9,700,411 B2 | 7/2017 | Klima et al. |
| 9,730,791 B2 | 8/2017 | Ratz et al. |
| 9,730,794 B2 | 8/2017 | Carpentier et al. |
| 9,750,605 B2 | 9/2017 | Ganesan et al. |
| 9,750,606 B2 | 9/2017 | Ganesan et al. |
| 9,750,607 B2 | 9/2017 | Ganesan et al. |
| 9,763,657 B2 | 9/2017 | Hacohen et al. |
| 9,763,658 B2 | 9/2017 | Eigler et al. |
| 9,763,782 B2 | 9/2017 | Solem et al. |
| 9,770,328 B2 | 9/2017 | Macoviak et al. |
| 9,788,931 B2 | 10/2017 | Giordano et al. |
| 9,801,717 B2 | 10/2017 | Edquist et al. |
| 9,827,092 B2 | 11/2017 | Vidlund et al. |
| 9,827,101 B2 | 11/2017 | Solem et al. |
| 9,833,313 B2 | 12/2017 | Board et al. |

(56) References Cited

U.S. PATENT DOCUMENTS

| | | | |
|---|---|---|---|
| 9,833,315 B2 | 12/2017 | Vidlund et al. | |
| 9,839,511 B2 | 12/2017 | Ma et al. | |
| 9,844,435 B2 | 12/2017 | Eidenschink | |
| 9,848,880 B2 | 12/2017 | Coleman et al. | |
| 9,848,983 B2 | 12/2017 | Lashinski et al. | |
| 9,861,477 B2 | 1/2018 | Backus et al. | |
| 9,861,480 B2 | 1/2018 | Zakai et al. | |
| 10,792,151 B2* | 10/2020 | Mauch | A61F 2/243 |
| 2001/0021872 A1 | 9/2001 | Bailey et al. | |
| 2001/0049492 A1 | 12/2001 | Frazier et al. | |
| 2002/0007219 A1 | 1/2002 | Merrill et al. | |
| 2002/0013571 A1 | 1/2002 | Goldfarb et al. | |
| 2002/0072792 A1 | 6/2002 | Burgermeister et al. | |
| 2002/0082637 A1 | 6/2002 | Lumauig | |
| 2002/0099439 A1 | 7/2002 | Schwartz et al. | |
| 2002/0138138 A1 | 9/2002 | Yang | |
| 2002/0151970 A1 | 10/2002 | Garrison et al. | |
| 2002/0173841 A1 | 11/2002 | Ortiz et al. | |
| 2003/0120340 A1 | 6/2003 | Liska et al. | |
| 2003/0139689 A1 | 7/2003 | Shturman et al. | |
| 2004/0006358 A1 | 1/2004 | Wulfman et al. | |
| 2004/0039412 A1 | 2/2004 | Isshiki et al. | |
| 2004/0044350 A1 | 3/2004 | Martin et al. | |
| 2004/0057955 A1 | 3/2004 | O'Brien et al. | |
| 2004/0082910 A1 | 4/2004 | Constantz et al. | |
| 2004/0092858 A1 | 5/2004 | Wilson et al. | |
| 2004/0092962 A1 | 5/2004 | Thornton et al. | |
| 2004/0092989 A1 | 5/2004 | Wilson et al. | |
| 2004/0106989 A1 | 6/2004 | Wilson et al. | |
| 2004/0117009 A1 | 6/2004 | Cali et al. | |
| 2004/0122510 A1 | 6/2004 | Sarac | |
| 2004/0127979 A1 | 7/2004 | Wilson et al. | |
| 2004/0127982 A1 | 7/2004 | Machold et al. | |
| 2004/0186558 A1 | 9/2004 | Pavcnik et al. | |
| 2004/0199191 A1 | 10/2004 | Schwartz | |
| 2004/0230117 A1 | 11/2004 | Tosaya et al. | |
| 2004/0230212 A1 | 11/2004 | Wulfman | |
| 2004/0230213 A1 | 11/2004 | Wulfman et al. | |
| 2004/0243162 A1 | 12/2004 | Wulfman et al. | |
| 2005/0007219 A1 | 1/2005 | Ma et al. | |
| 2005/0075662 A1 | 4/2005 | Pedersen et al. | |
| 2005/0075720 A1 | 4/2005 | Nguyen et al. | |
| 2005/0075727 A1 | 4/2005 | Wheatley | |
| 2005/0107661 A1 | 5/2005 | Lau et al. | |
| 2005/0137682 A1 | 6/2005 | Justino | |
| 2005/0137690 A1 | 6/2005 | Salahieh et al. | |
| 2005/0137691 A1 | 6/2005 | Salahieh et al. | |
| 2005/0137695 A1 | 6/2005 | Salahieh et al. | |
| 2005/0137697 A1 | 6/2005 | Salahieh et al. | |
| 2005/0137698 A1 | 6/2005 | Salahieh et al. | |
| 2005/0137700 A1 | 6/2005 | Spence et al. | |
| 2005/0137701 A1 | 6/2005 | Salahieh et al. | |
| 2005/0137702 A1 | 6/2005 | Haug et al. | |
| 2005/0228477 A1 | 10/2005 | Grainger et al. | |
| 2005/0267523 A1 | 12/2005 | Devellian et al. | |
| 2005/0273135 A1 | 12/2005 | Chanduszko | |
| 2006/0058872 A1 | 3/2006 | Salahieh et al. | |
| 2006/0106456 A9 | 5/2006 | Machold et al. | |
| 2006/0149360 A1 | 7/2006 | Schwammenthal et al. | |
| 2006/0167543 A1 | 7/2006 | Bailey et al. | |
| 2006/0195183 A1 | 8/2006 | Navia et al. | |
| 2006/0253191 A1 | 11/2006 | Salahieh et al. | |
| 2006/0287719 A1 | 12/2006 | Rowe et al. | |
| 2007/0056346 A1 | 3/2007 | Spencer et al. | |
| 2007/0061010 A1 | 3/2007 | Hauser et al. | |
| 2007/0073391 A1 | 3/2007 | Bourang et al. | |
| 2007/0078302 A1 | 4/2007 | Ortiz et al. | |
| 2007/0088431 A1 | 4/2007 | Bourang et al. | |
| 2007/0142906 A1 | 6/2007 | Figulla et al. | |
| 2007/0173932 A1 | 7/2007 | Cali et al. | |
| 2007/0203575 A1 | 8/2007 | Forster et al. | |
| 2008/0065011 A1 | 3/2008 | Marchand et al. | |
| 2008/0071369 A1 | 3/2008 | Tuval et al. | |
| 2008/0082166 A1 | 4/2008 | Styrc et al. | |
| 2008/0103586 A1 | 5/2008 | Styrc et al. | |
| 2008/0140189 A1 | 6/2008 | Nguyen et al. | |
| 2008/0208332 A1 | 8/2008 | Lamphere et al. | |
| 2008/0221672 A1 | 9/2008 | Lamphere et al. | |
| 2008/0234728 A1 | 9/2008 | Starksen et al. | |
| 2008/0243245 A1 | 10/2008 | Thambar et al. | |
| 2008/0243246 A1 | 10/2008 | Ryan et al. | |
| 2009/0054969 A1 | 2/2009 | Salahieh et al. | |
| 2009/0076586 A1 | 3/2009 | Hauser et al. | |
| 2009/0076598 A1 | 3/2009 | Salahieh et al. | |
| 2009/0093670 A1 | 4/2009 | Annest et al. | |
| 2009/0157174 A1 | 6/2009 | Yoganathan et al. | |
| 2009/0164006 A1 | 6/2009 | Seguin et al. | |
| 2009/0198315 A1 | 8/2009 | Boudjemline | |
| 2009/0216312 A1 | 8/2009 | Straubinger et al. | |
| 2009/0240320 A1 | 9/2009 | Tuval et al. | |
| 2009/0259292 A1 | 10/2009 | Bonhoeffer | |
| 2009/0259306 A1 | 10/2009 | Rowe | |
| 2009/0264997 A1 | 10/2009 | Salahieh et al. | |
| 2009/0276040 A1 | 11/2009 | Rowe et al. | |
| 2009/0281609 A1 | 11/2009 | Benichou et al. | |
| 2009/0281618 A1 | 11/2009 | Hill et al. | |
| 2009/0292350 A1 | 11/2009 | Eberhardt et al. | |
| 2009/0306768 A1 | 12/2009 | Quadri | |
| 2009/0319037 A1 | 12/2009 | Rowe et al. | |
| 2009/0319038 A1 | 12/2009 | Gurskis et al. | |
| 2010/0016958 A1 | 1/2010 | St. Goar et al. | |
| 2010/0023115 A1 | 1/2010 | Robaina et al. | |
| 2010/0023117 A1 | 1/2010 | Yoganathan et al. | |
| 2010/0030330 A1 | 2/2010 | Bobo et al. | |
| 2010/0049313 A1 | 2/2010 | Alon et al. | |
| 2010/0076548 A1 | 3/2010 | Konno | |
| 2010/0082094 A1 | 4/2010 | Quadri et al. | |
| 2010/0094411 A1 | 4/2010 | Tuval et al. | |
| 2010/0100167 A1 | 4/2010 | Bortlein et al. | |
| 2010/0121436 A1 | 5/2010 | Tuval et al. | |
| 2010/0185275 A1 | 7/2010 | Richter et al. | |
| 2010/0191326 A1* | 7/2010 | Alkhatib | A61F 2/2439 623/2.11 |
| 2010/0217382 A1 | 8/2010 | Chau et al. | |
| 2010/0249915 A1 | 9/2010 | Zhang | |
| 2010/0249923 A1 | 9/2010 | Alkhatib et al. | |
| 2010/0286768 A1 | 11/2010 | Alkhatib | |
| 2010/0298929 A1 | 11/2010 | Thornton et al. | |
| 2010/0298931 A1 | 11/2010 | Quadri et al. | |
| 2010/0312333 A1 | 12/2010 | Navia et al. | |
| 2010/0324554 A1 | 12/2010 | Gifford et al. | |
| 2011/0004296 A1 | 1/2011 | Lutter et al. | |
| 2011/0015722 A1 | 1/2011 | Hauser et al. | |
| 2011/0022166 A1 | 1/2011 | Dahlgren et al. | |
| 2011/0029071 A1 | 2/2011 | Zlotnick et al. | |
| 2011/0029072 A1 | 2/2011 | Gabbay | |
| 2011/0040374 A1 | 2/2011 | Goetz et al. | |
| 2011/0040375 A1 | 2/2011 | Letac et al. | |
| 2011/0066231 A1 | 3/2011 | Cartledge et al. | |
| 2011/0066233 A1 | 3/2011 | Thornton et al. | |
| 2011/0082464 A1 | 4/2011 | Douk et al. | |
| 2011/0112632 A1 | 5/2011 | Chau et al. | |
| 2011/0137397 A1 | 6/2011 | Chau et al. | |
| 2011/0137409 A1 | 6/2011 | Yang et al. | |
| 2011/0137410 A1 | 6/2011 | Hacohen | |
| 2011/0153008 A1 | 6/2011 | Marchand et al. | |
| 2011/0172784 A1 | 7/2011 | Richter et al. | |
| 2011/0184512 A1 | 7/2011 | Webler et al. | |
| 2011/0208293 A1 | 8/2011 | Tabor | |
| 2011/0224785 A1 | 9/2011 | Hacohen | |
| 2011/0264202 A1 | 10/2011 | Murray, III et al. | |
| 2011/0282425 A1 | 11/2011 | Dwork | |
| 2011/0301685 A1 | 12/2011 | Kao | |
| 2011/0319988 A1 | 12/2011 | Schankereli et al. | |
| 2012/0022639 A1 | 1/2012 | Hacohen et al. | |
| 2012/0035703 A1 | 2/2012 | Lutter et al. | |
| 2012/0035713 A1 | 2/2012 | Lutter et al. | |
| 2012/0053680 A1 | 3/2012 | Bolling et al. | |
| 2012/0053682 A1 | 3/2012 | Kovalsky et al. | |
| 2012/0078347 A1 | 3/2012 | Braido et al. | |
| 2012/0078360 A1 | 3/2012 | Rafiee | |
| 2012/0101571 A1 | 4/2012 | Thambar et al. | |
| 2012/0165930 A1 | 6/2012 | Gifford, III et al. | |
| 2012/0179239 A1 | 7/2012 | Quadri | |

(56) References Cited

U.S. PATENT DOCUMENTS

| | | |
|---|---|---|
| 2012/0179244 A1 | 7/2012 | Schankereli et al. |
| 2012/0203336 A1 | 8/2012 | Annest |
| 2012/0283824 A1 | 11/2012 | Lutter et al. |
| 2013/0079872 A1* | 3/2013 | Gallagher ............ A61F 2/2436 623/2.11 |
| 2013/0172978 A1 | 7/2013 | Vidlund et al. |
| 2013/0190860 A1 | 7/2013 | Sundt, III |
| 2013/0190861 A1 | 7/2013 | Chau et al. |
| 2013/0197354 A1 | 8/2013 | Maschke et al. |
| 2013/0197630 A1 | 8/2013 | Azarnoush |
| 2013/0204356 A1 | 8/2013 | Dwork et al. |
| 2013/0204358 A1 | 8/2013 | Matheny |
| 2013/0226289 A1 | 8/2013 | Shaolian et al. |
| 2013/0226290 A1 | 8/2013 | Yellin et al. |
| 2013/0231735 A1 | 9/2013 | Deem et al. |
| 2013/0238089 A1 | 9/2013 | Lichtenstein et al. |
| 2013/0244927 A1 | 9/2013 | Lal et al. |
| 2013/0253641 A1 | 9/2013 | Lattouf |
| 2013/0253642 A1 | 9/2013 | Brecker |
| 2013/0253643 A1 | 9/2013 | Rolando et al. |
| 2013/0259337 A1 | 10/2013 | Guhring et al. |
| 2013/0261737 A1 | 10/2013 | Costello |
| 2013/0261738 A1 | 10/2013 | Clague et al. |
| 2013/0261739 A1 | 10/2013 | Kuehn |
| 2013/0261741 A1 | 10/2013 | Accola |
| 2013/0268066 A1 | 10/2013 | Rowe |
| 2013/0274870 A1 | 10/2013 | Lombardi et al. |
| 2013/0282059 A1 | 10/2013 | Ketai et al. |
| 2013/0282060 A1 | 10/2013 | Tuval |
| 2013/0282110 A1 | 10/2013 | Schweich, Jr. et al. |
| 2013/0289642 A1 | 10/2013 | Hedberg et al. |
| 2013/0289717 A1 | 10/2013 | Solem |
| 2013/0289718 A1 | 10/2013 | Tsukashima et al. |
| 2013/0296851 A1 | 11/2013 | Boronyak et al. |
| 2013/0296999 A1 | 11/2013 | Burriesci et al. |
| 2013/0304180 A1 | 11/2013 | Green et al. |
| 2013/0304181 A1 | 11/2013 | Green et al. |
| 2013/0304197 A1 | 11/2013 | Buchbinder et al. |
| 2013/0304198 A1 | 11/2013 | Solem |
| 2013/0304200 A1 | 11/2013 | Mclean et al. |
| 2013/0309292 A1 | 11/2013 | Andersen |
| 2013/0310436 A1 | 11/2013 | Lowes et al. |
| 2013/0310925 A1 | 11/2013 | Eliasen et al. |
| 2013/0310928 A1 | 11/2013 | Morriss et al. |
| 2013/0317603 A1 | 11/2013 | Mclean et al. |
| 2013/0325110 A1 | 12/2013 | Khalil et al. |
| 2013/0325114 A1 | 12/2013 | Mclean et al. |
| 2013/0331864 A1 | 12/2013 | Jelich et al. |
| 2013/0338684 A1 | 12/2013 | Hausen |
| 2013/0338763 A1 | 12/2013 | Rowe et al. |
| 2013/0345797 A1 | 12/2013 | Dahlgren et al. |
| 2013/0345803 A1 | 12/2013 | Bergheim, III |
| 2014/0005778 A1 | 1/2014 | Buchbinder et al. |
| 2014/0018906 A1 | 1/2014 | Rafiee |
| 2014/0018913 A1 | 1/2014 | Cartledge et al. |
| 2014/0023261 A1 | 1/2014 | Watanabe et al. |
| 2014/0025164 A1 | 1/2014 | Montorfano et al. |
| 2014/0031928 A1 | 1/2014 | Murphy et al. |
| 2014/0046219 A1 | 2/2014 | Sauter et al. |
| 2014/0046436 A1 | 2/2014 | Kheradvar |
| 2014/0052237 A1 | 2/2014 | Lane et al. |
| 2014/0052240 A1 | 2/2014 | Zhang |
| 2014/0056906 A1 | 2/2014 | Yue et al. |
| 2014/0066895 A1 | 3/2014 | Kipperman |
| 2014/0067048 A1 | 3/2014 | Chau et al. |
| 2014/0067052 A1 | 3/2014 | Chau et al. |
| 2014/0067054 A1 | 3/2014 | Chau et al. |
| 2014/0088071 A1 | 3/2014 | Nakai et al. |
| 2014/0088680 A1 | 3/2014 | Costello et al. |
| 2014/0088693 A1 | 3/2014 | Seguin et al. |
| 2014/0088695 A1 | 3/2014 | Figulla et al. |
| 2014/0094906 A1 | 4/2014 | Spence et al. |
| 2014/0107758 A1* | 4/2014 | Glazier ................ A61F 2/2436 623/1.12 |
| 2014/0107775 A1 | 4/2014 | Hjelle et al. |
| 2014/0114404 A1 | 4/2014 | Gammie et al. |
| 2014/0114407 A1 | 4/2014 | Rajamannan |
| 2014/0121763 A1 | 5/2014 | Duffy et al. |
| 2014/0128965 A1 | 5/2014 | Rafiee |
| 2014/0135913 A1 | 5/2014 | Lichtenstein et al. |
| 2014/0163652 A1 | 6/2014 | Witzel et al. |
| 2014/0163668 A1 | 6/2014 | Rafiee |
| 2014/0172076 A1 | 6/2014 | Jonsson et al. |
| 2014/0172084 A1 | 6/2014 | Callas et al. |
| 2014/0172085 A1 | 6/2014 | Quadri et al. |
| 2014/0172086 A1 | 6/2014 | Quadri et al. |
| 2014/0179993 A1 | 6/2014 | Alexander et al. |
| 2014/0180401 A1 | 6/2014 | Quill et al. |
| 2014/0188108 A1 | 7/2014 | Goodine et al. |
| 2014/0188215 A1 | 7/2014 | Hlavka et al. |
| 2014/0194920 A1 | 7/2014 | Krahbichler |
| 2014/0194976 A1 | 7/2014 | Starksen et al. |
| 2014/0200397 A1 | 7/2014 | Raman et al. |
| 2014/0200649 A1 | 7/2014 | Essinger et al. |
| 2014/0200657 A1 | 7/2014 | Maurer et al. |
| 2014/0200662 A1 | 7/2014 | Eftel et al. |
| 2014/0214159 A1 | 7/2014 | Vidlund et al. |
| 2014/0219524 A1 | 8/2014 | Takeguchi et al. |
| 2014/0222040 A1 | 8/2014 | Park et al. |
| 2014/0222138 A1 | 8/2014 | Machold et al. |
| 2014/0228942 A1 | 8/2014 | Krahbichler |
| 2014/0228946 A1 | 8/2014 | Chau et al. |
| 2014/0242086 A1 | 8/2014 | Lal et al. |
| 2014/0243860 A1 | 8/2014 | Morris et al. |
| 2014/0243954 A1 | 8/2014 | Shannon |
| 2014/0243964 A1 | 8/2014 | Venkatasubramanian |
| 2014/0249621 A1 | 9/2014 | Eidenschink |
| 2014/0257101 A1 | 9/2014 | Gaudiani |
| 2014/0257466 A1 | 9/2014 | Board et al. |
| 2014/0257467 A1 | 9/2014 | Lane et al. |
| 2014/0257473 A1 | 9/2014 | Rajamannan |
| 2014/0257475 A1 | 9/2014 | Gross et al. |
| 2014/0275757 A1 | 9/2014 | Goodwin et al. |
| 2014/0276395 A1 | 9/2014 | Wilson et al. |
| 2014/0276609 A1 | 9/2014 | Magee et al. |
| 2014/0276782 A1 | 9/2014 | Paskar |
| 2014/0276971 A1 | 9/2014 | Kovach |
| 2014/0277119 A1 | 9/2014 | Akpinar |
| 2014/0277390 A1 | 9/2014 | Ratz et al. |
| 2014/0277404 A1 | 9/2014 | Wilson et al. |
| 2014/0277405 A1 | 9/2014 | Wilson et al. |
| 2014/0277406 A1 | 9/2014 | Arcidi |
| 2014/0277407 A1 | 9/2014 | Dale et al. |
| 2014/0277408 A1 | 9/2014 | Folan |
| 2014/0277409 A1 | 9/2014 | Bortlein et al. |
| 2014/0277410 A1 | 9/2014 | Bortlein et al. |
| 2014/0277411 A1 | 9/2014 | Bortlein et al. |
| 2014/0277412 A1 | 9/2014 | Bortlein et al. |
| 2014/0277420 A1 | 9/2014 | Migliazza et al. |
| 2014/0277422 A1 | 9/2014 | Ratz et al. |
| 2014/0288480 A1 | 9/2014 | Zimmerman et al. |
| 2014/0296878 A1 | 10/2014 | Oz et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296975 A1 | 10/2014 | Tegels et al. |
| 2014/0303719 A1 | 10/2014 | Cox et al. |
| 2014/0303721 A1 | 10/2014 | Fung et al. |
| 2014/0309727 A1 | 10/2014 | Lamelas et al. |
| 2014/0309730 A1 | 10/2014 | Alon et al. |
| 2014/0309731 A1 | 10/2014 | Quadri et al. |
| 2014/0309732 A1 | 10/2014 | Solem |
| 2014/0316516 A1 | 10/2014 | Vidlund et al. |
| 2014/0324164 A1 | 10/2014 | Gross et al. |
| 2014/0358222 A1 | 12/2014 | Gorman, III et al. |
| 2014/0358224 A1 | 12/2014 | Tegels et al. |
| 2014/0364944 A1 | 12/2014 | Lutter et al. |
| 2014/0371843 A1 | 12/2014 | Wilson et al. |
| 2014/0371844 A1 | 12/2014 | Dale et al. |
| 2014/0371846 A1 | 12/2014 | Wilson et al. |
| 2014/0379074 A1 | 12/2014 | Spence et al. |
| 2014/0379076 A1 | 12/2014 | Vidlund et al. |
| 2015/0005874 A1 | 1/2015 | Vidlund et al. |
| 2015/0005875 A1 | 1/2015 | Tuval et al. |

(56) References Cited

U.S. PATENT DOCUMENTS

| | | |
|---|---|---|
| 2015/0025623 A1 | 1/2015 | Granada et al. |
| 2015/0032127 A1 | 1/2015 | Gammie et al. |
| 2015/0045878 A1 | 2/2015 | Rowe |
| 2015/0066140 A1 | 3/2015 | Quadri et al. |
| 2015/0094802 A1 | 4/2015 | Buchbinder et al. |
| 2015/0094803 A1 | 4/2015 | Navia |
| 2015/0100116 A1 | 4/2015 | Mohl et al. |
| 2015/0112427 A1 | 4/2015 | Schweich, Jr. et al. |
| 2015/0112429 A1 | 4/2015 | Khairkhahan et al. |
| 2015/0112433 A1 | 4/2015 | Schweich, Jr. et al. |
| 2015/0119978 A1 | 4/2015 | Tegels et al. |
| 2015/0119981 A1 | 4/2015 | Khairkhahan et al. |
| 2015/0119982 A1 | 4/2015 | Quill et al. |
| 2015/0127091 A1 | 5/2015 | Cecere et al. |
| 2015/0127096 A1 | 5/2015 | Rowe et al. |
| 2015/0142101 A1 | 5/2015 | Coleman et al. |
| 2015/0142103 A1 | 5/2015 | Vidlund |
| 2015/0142105 A1 | 5/2015 | Bolling et al. |
| 2015/0150678 A1 | 6/2015 | Brecker |
| 2015/0157458 A1 | 6/2015 | Thambar et al. |
| 2015/0157459 A1 | 6/2015 | Macoviak et al. |
| 2015/0164637 A1 | 6/2015 | Khairkhahan et al. |
| 2015/0164641 A1 | 6/2015 | Annest |
| 2015/0173897 A1 | 6/2015 | Raanani et al. |
| 2015/0173898 A1 | 6/2015 | Drasler et al. |
| 2015/0173900 A1 | 6/2015 | Hauser et al. |
| 2015/0190229 A1 | 7/2015 | Seguin |
| 2015/0196390 A1 | 7/2015 | Ma et al. |
| 2015/0196393 A1 | 7/2015 | Vidlund et al. |
| 2015/0202043 A1 | 7/2015 | Zakai et al. |
| 2015/0209137 A1 | 7/2015 | Quadri et al. |
| 2015/0209139 A1 | 7/2015 | Granada et al. |
| 2015/0216655 A1 | 8/2015 | Lane et al. |
| 2015/0216661 A1 | 8/2015 | Hacohen et al. |
| 2015/0223802 A1 | 8/2015 | Tegzes |
| 2015/0223934 A1 | 8/2015 | Vidlund et al. |
| 2015/0223935 A1 | 8/2015 | Subramanian et al. |
| 2015/0230920 A1 | 8/2015 | Alfieri et al. |
| 2015/0230921 A1 | 8/2015 | Chau et al. |
| 2015/0238312 A1 | 8/2015 | Lashinski |
| 2015/0238313 A1 | 8/2015 | Spence et al. |
| 2015/0250590 A1 | 9/2015 | Gries et al. |
| 2015/0257877 A1 | 9/2015 | Hernandez |
| 2015/0257878 A1 | 9/2015 | Lane et al. |
| 2015/0257879 A1 | 9/2015 | Bortlein et al. |
| 2015/0257881 A1 | 9/2015 | Bortlein et al. |
| 2015/0257882 A1 | 9/2015 | Bortlein et al. |
| 2015/0272737 A1 | 10/2015 | Dale et al. |
| 2015/0305861 A1 | 10/2015 | Annest |
| 2015/0305864 A1 | 10/2015 | Quadri et al. |
| 2015/0313739 A1 | 11/2015 | Hummen et al. |
| 2015/0320553 A1 | 11/2015 | Chau et al. |
| 2015/0327999 A1 | 11/2015 | Board et al. |
| 2015/0328000 A1 | 11/2015 | Ratz et al. |
| 2015/0342733 A1 | 12/2015 | Alkhatib et al. |
| 2015/0351906 A1 | 12/2015 | Hammer et al. |
| 2015/0351908 A1 | 12/2015 | Keranen et al. |
| 2015/0359628 A1 | 12/2015 | Keranen |
| 2015/0359629 A1 | 12/2015 | Ganesan et al. |
| 2015/0359631 A1 | 12/2015 | Sheahan et al. |
| 2015/0366666 A1 | 12/2015 | Khairkhahan et al. |
| 2015/0374495 A1 | 12/2015 | Ruyra Baliarda et al. |
| 2016/0000983 A1 | 1/2016 | Mohl et al. |
| 2016/0015513 A1 | 1/2016 | Lashinski et al. |
| 2016/0015514 A1 | 1/2016 | Lashinski et al. |
| 2016/0015515 A1 | 1/2016 | Lashinski et al. |
| 2016/0015543 A1 | 1/2016 | Perouse et al. |
| 2016/0030171 A1 | 2/2016 | Quijano et al. |
| 2016/0038246 A1 | 2/2016 | Wang et al. |
| 2016/0038280 A1 | 2/2016 | Morriss et al. |
| 2016/0038283 A1 | 2/2016 | Divekar et al. |
| 2016/0038286 A1 | 2/2016 | Yellin et al. |
| 2016/0074160 A1 | 3/2016 | Christianson et al. |
| 2016/0106539 A1 | 4/2016 | Buchbinder et al. |
| 2016/0113764 A1 | 4/2016 | Sheahan et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0120643 A1 | 5/2016 | Kupumbati |
| 2016/0143730 A1 | 5/2016 | Kheradvar |
| 2016/0151154 A1 | 6/2016 | Gorman, III et al. |
| 2016/0151156 A1 | 6/2016 | Seguin et al. |
| 2016/0151552 A1 | 6/2016 | Solem |
| 2016/0157999 A1 | 6/2016 | Lane et al. |
| 2016/0158000 A1 | 6/2016 | Granada et al. |
| 2016/0158001 A1 | 6/2016 | Wallace et al. |
| 2016/0158002 A1 | 6/2016 | Wallace et al. |
| 2016/0158003 A1 | 6/2016 | Wallace et al. |
| 2016/0184095 A1 | 6/2016 | Spence et al. |
| 2016/0206280 A1 | 7/2016 | Vidlund et al. |
| 2016/0206424 A1 | 7/2016 | Al-Jilaihawi et al. |
| 2016/0262881 A1 | 9/2016 | Schankereli et al. |
| 2016/0262884 A1* | 9/2016 | Lombardi ............. A61F 2/2412 |
| 2016/0317290 A1 | 11/2016 | Chau et al. |
| 2017/0079790 A1 | 3/2017 | Vidlund et al. |
| 2017/0100248 A1 | 4/2017 | Tegels et al. |
| 2017/0100250 A1 | 4/2017 | Marsot et al. |
| 2017/0119526 A1 | 5/2017 | Luong et al. |
| 2017/0128198 A1 | 5/2017 | Cartledge et al. |
| 2017/0128205 A1 | 5/2017 | Tamir et al. |
| 2017/0128206 A1 | 5/2017 | Rafiee et al. |
| 2017/0128208 A1 | 5/2017 | Christianson et al. |
| 2017/0156860 A1 | 6/2017 | Lashinski |
| 2017/0165054 A1 | 6/2017 | Benson et al. |
| 2017/0165055 A1 | 6/2017 | Hauser et al. |
| 2017/0165064 A1 | 6/2017 | Nyuli et al. |
| 2017/0172737 A1 | 6/2017 | Kuetting et al. |
| 2017/0181851 A1 | 6/2017 | Annest |
| 2017/0189177 A1 | 7/2017 | Schweich, Jr. et al. |
| 2017/0189179 A1 | 7/2017 | Ratz et al. |
| 2017/0189180 A1 | 7/2017 | Alkhatib |
| 2017/0189181 A1 | 7/2017 | Alkhatib et al. |
| 2017/0196688 A1 | 7/2017 | Christianson et al. |
| 2017/0231762 A1 | 8/2017 | Quadri et al. |
| 2017/0231763 A1 | 8/2017 | Yellin et al. |
| 2017/0258585 A1 | 9/2017 | Marquez et al. |
| 2017/0266001 A1 | 9/2017 | Vidlund et al. |
| 2017/0281345 A1 | 10/2017 | Yang et al. |
| 2017/0290659 A1 | 10/2017 | Ulmer et al. |
| 2017/0296338 A1 | 10/2017 | Cambell et al. |
| 2017/0296339 A1 | 10/2017 | Thambar et al. |
| 2017/0319333 A1 | 11/2017 | Tegels et al. |
| 2017/0325842 A1 | 11/2017 | Siegel |
| 2017/0325941 A1 | 11/2017 | Wallace et al. |
| 2017/0325945 A1 | 11/2017 | Dale et al. |
| 2017/0325948 A1 | 11/2017 | Wallace et al. |
| 2017/0325949 A1 | 11/2017 | Rodgers et al. |
| 2017/0325953 A1 | 11/2017 | Klima et al. |
| 2017/0325954 A1 | 11/2017 | Perszyk |
| 2017/0333186 A1 | 11/2017 | Spargias |
| 2017/0333188 A1 | 11/2017 | Carpentier et al. |
| 2017/0340440 A1 | 11/2017 | Ratz et al. |
| 2017/0348097 A1 | 12/2017 | Taft et al. |
| 2017/0348098 A1 | 12/2017 | Rowe et al. |
| 2017/0348100 A1 | 12/2017 | Lane et al. |
| 2017/0354496 A1 | 12/2017 | Quadri et al. |
| 2017/0354497 A1 | 12/2017 | Quadri et al. |
| 2017/0354499 A1 | 12/2017 | Granada et al. |
| 2017/0360426 A1 | 12/2017 | Hacohen et al. |
| 2017/0360549 A1 | 12/2017 | Lashinski et al. |
| 2017/0360558 A1 | 12/2017 | Ma |
| 2017/0360585 A1 | 12/2017 | White |
| 2017/0361065 A1 | 12/2017 | Legaspi et al. |

FOREIGN PATENT DOCUMENTS

| | | |
|---|---|---|
| CN | 101291637 A | 10/2008 |
| CN | 103096844 A | 5/2013 |
| CN | 103491900 A | 1/2014 |
| CN | 105025848 A | 11/2015 |
| CN | 105578989 A | 5/2016 |
| CN | 106580531 A | 4/2017 |
| DE | 19605042 A1 | 1/1998 |
| DE | 102006052564 B3 | 12/2007 |

(56) References Cited

FOREIGN PATENT DOCUMENTS

| | | |
|---|---|---|
| EP | 186104 A2 | 7/1986 |
| EP | 1512383 A2 | 3/2005 |
| EP | 1545371 A2 | 6/2005 |
| EP | 1551274 A2 | 7/2005 |
| EP | 1629794 A2 | 3/2006 |
| EP | 1646332 A2 | 4/2006 |
| EP | 1702247 A2 | 9/2006 |
| EP | 1734903 A1 | 12/2006 |
| EP | 1891914 | 2/2008 |
| EP | 2026280 A1 | 2/2009 |
| EP | 2037829 A2 | 3/2009 |
| EP | 2081519 A2 | 7/2009 |
| EP | 2111190 A2 | 10/2009 |
| EP | 2142143 A2 | 1/2010 |
| EP | 2167742 A1 | 3/2010 |
| EP | 2278944 A2 | 2/2011 |
| EP | 2306821 A1 | 4/2011 |
| EP | 2327429 A1 | 6/2011 |
| EP | 2400924 | 1/2012 |
| EP | 2400926 A2 | 1/2012 |
| EP | 2410947 A1 | 2/2012 |
| EP | 2416739 A2 | 2/2012 |
| EP | 2419050 | 2/2012 |
| EP | 2444031 A2 | 4/2012 |
| EP | 2488126 A1 | 8/2012 |
| EP | 2509538 A2 | 10/2012 |
| EP | 2549955 A1 | 1/2013 |
| EP | 2549956 A1 | 1/2013 |
| EP | 2566416 A1 | 3/2013 |
| EP | 2586492 A1 | 5/2013 |
| EP | 2618784 A2 | 7/2013 |
| EP | 2623068 A1 | 8/2013 |
| EP | 2626013 A2 | 8/2013 |
| EP | 2629699 A1 | 8/2013 |
| EP | 2633457 A1 | 9/2013 |
| EP | 2637659 A1 | 9/2013 |
| EP | 2641569 A1 | 9/2013 |
| EP | 2644158 | 10/2013 |
| EP | 2654624 A1 | 10/2013 |
| EP | 2656794 A1 | 10/2013 |
| EP | 2656795 A1 | 10/2013 |
| EP | 2656796 A1 | 10/2013 |
| EP | 2667823 A1 | 12/2013 |
| EP | 2670358 A2 | 12/2013 |
| EP | 2676640 A1 | 12/2013 |
| EP | 2688041 A2 | 1/2014 |
| EP | 2695586 | 2/2014 |
| EP | 2697721 A2 | 2/2014 |
| EP | 2713953 A1 | 4/2014 |
| EP | 2714068 A2 | 4/2014 |
| EP | 2723272 A2 | 4/2014 |
| EP | 2723273 A2 | 4/2014 |
| EP | 2723277 A1 | 4/2014 |
| EP | 2739214 A2 | 6/2014 |
| EP | 2741711 A2 | 6/2014 |
| EP | 2750630 A1 | 7/2014 |
| EP | 2750631 A1 | 7/2014 |
| EP | 2755562 A1 | 7/2014 |
| EP | 2755602 A1 | 7/2014 |
| EP | 2757962 A1 | 7/2014 |
| EP | 2777616 A1 | 9/2014 |
| EP | 2777617 A1 | 9/2014 |
| EP | 2782523 A1 | 10/2014 |
| EP | 2785282 A1 | 10/2014 |
| EP | 2786817 | 10/2014 |
| EP | 2790609 A1 | 10/2014 |
| EP | 2793751 A1 | 10/2014 |
| EP | 2809263 A1 | 12/2014 |
| EP | 2810620 A1 | 12/2014 |
| EP | 2814428 A1 | 12/2014 |
| EP | 2814429 A1 | 12/2014 |
| EP | 2819617 A1 | 1/2015 |
| EP | 2819618 A1 | 1/2015 |
| EP | 2819619 A1 | 1/2015 |
| EP | 2717803 | 2/2015 |
| EP | 2833836 A1 | 2/2015 |
| EP | 2838475 A1 | 2/2015 |
| EP | 2839815 | 2/2015 |
| EP | 2844190 | 3/2015 |
| EP | 2849680 A2 | 3/2015 |
| EP | 2849681 A1 | 3/2015 |
| EP | 2852354 A2 | 4/2015 |
| EP | 2854719 | 4/2015 |
| EP | 2870933 | 5/2015 |
| EP | 2873011 A1 | 5/2015 |
| EP | 2875797 A1 | 5/2015 |
| EP | 2760375 | 6/2015 |
| EP | 2882374 A1 | 6/2015 |
| EP | 2886082 | 6/2015 |
| EP | 2886083 A1 | 6/2015 |
| EP | 2886084 A1 | 6/2015 |
| EP | 2895111 A2 | 7/2015 |
| EP | 2901966 A1 | 8/2015 |
| EP | 2907479 A1 | 8/2015 |
| EP | 2945572 A1 | 11/2015 |
| EP | 2948094 A1 | 12/2015 |
| EP | 2948102 A1 | 12/2015 |
| EP | 2964152 A1 | 1/2016 |
| EP | 2967859 A1 | 1/2016 |
| EP | 2967860 A1 | 1/2016 |
| EP | 2967866 A2 | 1/2016 |
| EP | 2968847 A1 | 1/2016 |
| EP | 2981208 | 2/2016 |
| EP | 2982336 A1 | 2/2016 |
| EP | 2999433 A1 | 3/2016 |
| EP | 3003187 A1 | 4/2016 |
| EP | 3003219 A1 | 4/2016 |
| EP | 3003220 A1 | 4/2016 |
| EP | 3010447 A1 | 4/2016 |
| EP | 3013281 A1 | 5/2016 |
| EP | 3017792 A1 | 5/2016 |
| EP | 3021792 A2 | 5/2016 |
| EP | 3023117 A1 | 5/2016 |
| EP | 3027143 A1 | 6/2016 |
| EP | 3033048 A2 | 6/2016 |
| EP | 3037064 A1 | 6/2016 |
| EP | 3079633 | 10/2016 |
| EP | 3229736 | 11/2016 |
| EP | 2470119 | 5/2017 |
| EP | 2999436 | 5/2017 |
| EP | 3184081 | 6/2017 |
| EP | 3191027 | 7/2017 |
| EP | 2611389 | 8/2017 |
| EP | 3082656 | 8/2017 |
| EP | 3206628 | 8/2017 |
| EP | 2010103 | 9/2017 |
| EP | 2509538 | 9/2017 |
| EP | 3223751 | 10/2017 |
| EP | 3027144 | 11/2017 |
| EP | 3110368 | 11/2017 |
| EP | 3110369 | 11/2017 |
| EP | 3132773 | 11/2017 |
| EP | 3245980 | 11/2017 |
| EP | 3250154 | 12/2017 |
| EP | 3256074 | 12/2017 |
| EP | 3256077 | 12/2017 |
| EP | 3258883 | 12/2017 |
| EP | 3270825 | 1/2018 |
| EP | 3273910 | 1/2018 |
| JP | 6504516 | 5/1994 |
| JP | H10258124 A | 9/1998 |
| JP | 2002509756 A | 4/2002 |
| JP | 2005280917 A | 10/2005 |
| JP | 2008528117 A | 7/2008 |
| JP | 2008541863 A | 11/2008 |
| JP | 2009195712 A | 9/2009 |
| JP | 2010518947 A | 6/2010 |
| JP | 5219518 B2 | 6/2013 |
| JP | 2013-540495 A | 11/2013 |
| WO | WO-1992017118 A1 | 10/1992 |
| WO | WO-1995016407 A1 | 6/1995 |
| WO | WO-1999004730 A1 | 2/1999 |
| WO | WO-1999039648 A1 | 8/1999 |
| WO | WO-1999049799 A1 | 10/1999 |

(56) References Cited

FOREIGN PATENT DOCUMENTS

| | | |
|---|---|---|
| WO | WO-2001010343 | 2/2001 |
| WO | WO-2002003892 A1 | 1/2002 |
| WO | WO-2002028421 A1 | 4/2002 |
| WO | WO-2002039908 A2 | 5/2002 |
| WO | WO-2003043685 A2 | 5/2003 |
| WO | WO-2004084746 A2 | 10/2004 |
| WO | WO-2004093728 A2 | 11/2004 |
| WO | WO-2004096097 A2 | 11/2004 |
| WO | WO-2004112657 A1 | 12/2004 |
| WO | WO-2005002466 A2 | 1/2005 |
| WO | WO-2005007219 A2 | 1/2005 |
| WO | WO-2005009285 A2 | 2/2005 |
| WO | WO-2005009506 A2 | 2/2005 |
| WO | WO-2005087140 A1 | 9/2005 |
| WO | WO-2006041877 A2 | 4/2006 |
| WO | WO-2006063199 A2 | 6/2006 |
| WO | WO-2007008371 A2 | 1/2007 |
| WO | WO-2007067820 A2 | 6/2007 |
| WO | WO2007098232 | 8/2007 |
| WO | WO-2008022077 A2 | 2/2008 |
| WO | WO-2008028569 A1 | 3/2008 |
| WO | WO-2008035337 A2 | 3/2008 |
| WO | 2008103722 | 8/2008 |
| WO | WO-2008103497 A2 | 8/2008 |
| WO | WO-2008129405 A2 | 10/2008 |
| WO | WO-2009045338 A1 | 4/2009 |
| WO | WO2009091509 | 7/2009 |
| WO | WO-2010006627 A1 | 1/2010 |
| WO | WO-2010008549 A1 | 1/2010 |
| WO | 2010/045297 A2 | 4/2010 |
| WO | WO-2010057262 A1 | 5/2010 |
| WO | WO-2010080594 A2 | 7/2010 |
| WO | WO-2010098857 A1 | 9/2010 |
| WO | WO-2010099032 A2 | 9/2010 |
| WO | WO-2010117680 A1 | 10/2010 |
| WO | WO2010121076 | 10/2010 |
| WO | WO2011025981 | 3/2011 |
| WO | WO-2011047168 A1 | 4/2011 |
| WO | WO-2011051043 A1 | 5/2011 |
| WO | WO-2011057087 A1 | 5/2011 |
| WO | WO-2011072084 A2 | 6/2011 |
| WO | 2011/094527 A1 | 8/2011 |
| WO | WO-2011106137 A1 | 9/2011 |
| WO | WO-2011106544 A1 | 9/2011 |
| WO | WO-2011111047 A2 | 9/2011 |
| WO | 2011144351 A2 | 11/2011 |
| WO | WO-2011137531 A1 | 11/2011 |
| WO | WO-2011139747 A1 | 11/2011 |
| WO | WO-2012011018 A1 | 1/2012 |
| WO | WO-2012011108 A2 | 1/2012 |
| WO | 2012/038550 A1 | 3/2012 |
| WO | WO-2012027487 A2 | 3/2012 |
| WO | WO-2012035279 A1 | 3/2012 |
| WO | WO-2012040655 A2 | 3/2012 |
| WO | WO-2012047644 A2 | 4/2012 |
| WO | WO2012052718 | 4/2012 |
| WO | WO-2012055498 A1 | 5/2012 |
| WO | WO-2012087842 A1 | 6/2012 |
| WO | WO-2012095455 A2 | 7/2012 |
| WO | WO-2012102928 A1 | 8/2012 |
| WO | WO-2012106602 A2 | 8/2012 |
| WO | WO-2012118508 A1 | 9/2012 |
| WO | WO-2012118816 A1 | 9/2012 |
| WO | WO-2012118894 A2 | 9/2012 |
| WO | WO-2012177942 A2 | 12/2012 |
| WO | WO-2013021374 A2 | 2/2013 |
| WO | WO-2013021375 A2 | 2/2013 |
| WO | WO-2013028387 A2 | 2/2013 |
| WO | WO-2013059743 A1 | 4/2013 |
| WO | WO-2013059747 A1 | 4/2013 |
| WO | WO-2013114214 A2 | 8/2013 |
| WO | WO-2013120181 A1 | 8/2013 |
| WO | WO-2013123059 A1 | 8/2013 |
| WO | WO-2013128432 A1 | 9/2013 |
| WO | WO-2013130641 A1 | 9/2013 |
| WO | WO-2013131925 A1 | 9/2013 |
| WO | WO-2013140318 A1 | 9/2013 |
| WO | WO-2013148017 A1 | 10/2013 |
| WO | WO-2013148018 A1 | 10/2013 |
| WO | WO-2013148019 A1 | 10/2013 |
| WO | WO-2013150512 A1 | 10/2013 |
| WO | WO-2013152161 A1 | 10/2013 |
| WO | WO-2013158613 A1 | 10/2013 |
| WO | WO-2013169448 A1 | 11/2013 |
| WO | WO-2013175468 A2 | 11/2013 |
| WO | WO-2013176583 A2 | 11/2013 |
| WO | WO-2013188077 A1 | 12/2013 |
| WO | WO-2013192107 A1 | 12/2013 |
| WO | WO-2014036113 A1 | 3/2014 |
| WO | WO-2014043527 A2 | 3/2014 |
| WO | WO-2014047111 A1 | 3/2014 |
| WO | WO-2014047325 A1 | 3/2014 |
| WO | WO-2014055981 A1 | 4/2014 |
| WO | WO-2014059432 A2 | 4/2014 |
| WO | WO-2014064694 A2 | 5/2014 |
| WO | WO-2014066365 A1 | 5/2014 |
| WO | WO-2014089424 A1 | 6/2014 |
| WO | WO-2014093861 A1 | 6/2014 |
| WO | WO-2014111918 A1 | 7/2014 |
| WO | WO-2014114794 A2 | 7/2014 |
| WO | WO-2014114795 A1 | 7/2014 |
| WO | WO-2014114796 A1 | 7/2014 |
| WO | WO-2014114798 A1 | 7/2014 |
| WO | WO-2014116502 A1 | 7/2014 |
| WO | WO-2014121280 A2 | 8/2014 |
| WO | WO-2014128705 A1 | 8/2014 |
| WO | WO-2014134277 A1 | 9/2014 |
| WO | WO-2014138194 A1 | 9/2014 |
| WO | WO-2014138284 A1 | 9/2014 |
| WO | WO-2014138482 A1 | 9/2014 |
| WO | WO-2014138868 A1 | 9/2014 |
| WO | WO-2014144100 A2 | 9/2014 |
| WO | WO-2014144937 A2 | 9/2014 |
| WO | WO-2014145338 A1 | 9/2014 |
| WO | WO-2014147336 A1 | 9/2014 |
| WO | WO-2014152306 A1 | 9/2014 |
| WO | WO-2014152375 A2 | 9/2014 |
| WO | WO-2014152503 A1 | 9/2014 |
| WO | WO-2014153544 A1 | 9/2014 |
| WO | 2014158958 A1 | 10/2014 |
| WO | WO-2014158617 A1 | 10/2014 |
| WO | WO-2014162181 A2 | 10/2014 |
| WO | WO-2014162306 A2 | 10/2014 |
| WO | WO-2014163705 A1 | 10/2014 |
| WO | WO-2014168655 A1 | 10/2014 |
| WO | WO-2014179391 A2 | 11/2014 |
| WO | WO-2014181336 A1 | 11/2014 |
| WO | WO-2014189974 A1 | 11/2014 |
| WO | 2014201380 A1 | 12/2014 |
| WO | WO-2014191994 A1 | 12/2014 |
| WO | WO-2014201384 A1 | 12/2014 |
| WO | WO-2014201452 A1 | 12/2014 |
| WO | WO-2014205064 A1 | 12/2014 |
| WO | WO-2014207699 A1 | 12/2014 |
| WO | WO-2014210124 A1 | 12/2014 |
| WO | WO-2014210299 A1 | 12/2014 |
| WO | WO-20144194178 | 12/2014 |
| WO | WO-2015009503 A2 | 1/2015 |
| WO | WO-2015020971 A1 | 2/2015 |
| WO | WO-2015028986 A1 | 3/2015 |
| WO | WO-2015051430 A1 | 4/2015 |
| WO | WO-2015052663 A1 | 4/2015 |
| WO | WO-2015057407 A1 | 4/2015 |
| WO | WO-2015057735 A1 | 4/2015 |
| WO | WO-2015057995 A2 | 4/2015 |
| WO | WO-2015061378 A1 | 4/2015 |
| WO | WO-2015061431 A1 | 4/2015 |
| WO | WO-2015061463 A1 | 4/2015 |
| WO | WO-2015061533 A1 | 4/2015 |
| WO | WO-2015075128 A1 | 5/2015 |
| WO | WO-2015081775 A1 | 6/2015 |
| WO | WO-2015089334 A1 | 6/2015 |
| WO | WO-2015092554 A2 | 6/2015 |
| WO | WO-2015120122 A2 | 8/2015 |

(56) References Cited

FOREIGN PATENT DOCUMENTS

| | | |
|---|---|---|
| WO | WO-2015125024 A2 | 8/2015 |
| WO | WO-2015127264 A1 | 8/2015 |
| WO | WO-2015127283 A1 | 8/2015 |
| WO | WO-2015128739 A2 | 9/2015 |
| WO | WO-2015128741 A2 | 9/2015 |
| WO | WO-2015128747 A2 | 9/2015 |
| WO | WO-2015132667 A1 | 9/2015 |
| WO | WO-2015132668 A1 | 9/2015 |
| WO | WO-2015135050 A1 | 9/2015 |
| WO | WO-2015142648 A1 | 9/2015 |
| WO | WO-2015142834 A1 | 9/2015 |
| WO | WO-2015148241 A1 | 10/2015 |
| WO | WO-2015171190 A1 | 11/2015 |
| WO | WO-2015171743 A2 | 11/2015 |
| WO | WO2015179181 | 11/2015 |
| WO | WO-2015191604 | 12/2015 |
| WO | WO-2015191839 A1 | 12/2015 |
| WO | WO-2015195823 A1 | 12/2015 |
| WO | WO-2016011185 A1 | 1/2016 |
| WO | WO-2016020918 A1 | 2/2016 |
| WO | WO-2016027272 A1 | 2/2016 |
| WO | WO-2016059533 A1 | 4/2016 |
| WO | WO-2016065158 A1 | 4/2016 |
| WO | WO-2016073741 A1 | 5/2016 |
| WO | WO-2016083551 A1 | 6/2016 |
| WO | WO-2016093877 A1 | 6/2016 |
| WO | WO-2016097337 A1 | 6/2016 |
| WO | WO-2016108181 A1 | 7/2016 |
| WO | WO2016133950 | 8/2016 |
| WO | WO2016150806 | 9/2016 |
| WO | WO2016201024 | 12/2016 |
| WO | WO2016209970 | 12/2016 |
| WO | WO2017011697 | 1/2017 |
| WO | 2017062640 | 4/2017 |
| WO | 2017087701 | 5/2017 |
| WO | 2017096157 | 6/2017 |
| WO | 2017100927 | 6/2017 |
| WO | 2017101232 | 6/2017 |
| WO | 2017117388 | 7/2017 |
| WO | 2017127939 | 8/2017 |
| WO | 2017136287 | 8/2017 |
| WO | 2017136596 | 8/2017 |
| WO | 2017165810 | 9/2017 |
| WO | 2017192960 | 11/2017 |
| WO | 2017196511 | 11/2017 |
| WO | 2017196909 | 11/2017 |
| WO | 2017196977 | 11/2017 |
| WO | 2017197064 | 11/2017 |
| WO | 2017197065 | 11/2017 |
| WO | 2017189040 | 12/2017 |
| WO | 2017218671 | 12/2017 |
| WO | 2018017886 | 1/2018 |
| WO | WO2018029680 | 2/2018 |

OTHER PUBLICATIONS

Bernard et al., "Aortic Valve Area Evolution After Percutaneous Aortic Valvuloplasty," European Heart Journal, Jul. 1990, vol. 11 (2), pp. 98-107.

BlueCross BlueShield of Northern Carolina Corporate Medical Policy "Balloon valvuloplasty, Percutaneous", (Jun. 1994).

Cimino et al., "Physics of Ultrasonic Surgery Using Tissue Fragmentation: Part I and Part II", Ultrasound in Medicine and Biologyl, Jun. 1996, vol. 22 (1), pp. 89-100, and pp. 101-117.

Cimino, "Ultrasonic Surgery: Power Quantification and Efficiency Optimization", Aesthetic Surgery Journal, Feb. 2001, pp. 233-241.

Cowell et al., "A Randomized Trial of Intensive Lipid-Lowering Therapy in Calcific Aortic Stenosis," NEJM, Jun. 2005, vol. 352 (23), pp. 2389-2397.

De Korte et al., "Characterization of Plaque Components and Vulnerability with Intravascular Ultrasound Elastography", Phys. Med. Biol., Feb. 2000, vol. 45, pp. 1465-1475.

European Search Report dated Mar. 13, 2015 for European Application. No. 05853460.3.

Feldman, "Restenosis Following Successful Balloon Valvuloplasty: Bone Formation in Aortic Valve Leaflets", Cathet Cardiovasc Diagn, May 1993, vol. 29 (1), pp. 1-7.

Fitzgerald et al., "Intravascular Sonotherapy Decreased Neointimal Hyperplasia After Stent Implantation in Swine", Circulation, Feb. 2001, vol. 103, pp. 1828-1831.

Freeman et al., "Ultrasonic Aortic Valve Decalcification: Serial Doppler Echocardiographic Follow Up", J Am Coll Cardiol., Sep. 1990, vol. 16 (3), pp. 623-630.

Greenleaf et al., "Selected Methods for Imaging Elastic Properties of Biological Tissues", Annu. Rev. Biomed. Eng., Apr. 2003, vol. 5, pp. 57-78.

Gunn et al., "New Developments in Therapeutic Ultrasound-Assisted Coronary Angioplasty", Curr Interv Cardiol Rep., Dec. 1990, vol. 1 (4), pp. 281-290.

Guzman et al., "Bioeffects Caused by Changes in Acoustic Cavitation Bubble Density and Cell Concentration: A Unified Explanation Based on Cell-to-Bubble Ratio and Blast Radius", Ultrasound in Med. & Biol., Mar. 2003, vol. 29 (8), pp. 1211-1222.

Hallgrimsson et al., "Chronic Non-Rheumatic Aortic Valvular Disease: a Population Study Based on Autopsies", J Chronic Dis., Jun. 1979, vol. 32 (5), pp. 355-363.

Isner et al., "Contrasting Histoarchitecture of Calcified Leaflets from Stenotic Bicuspid Versus Stenotic Tricuspid Aortic Valves", J Am Coll Cardiol., Apr. 1990, vol. 15 (5), p. 1104-1108.

Lung et al., "A Prospective Survey of Patients with Valvular Heart Disease in Europe: The Euro Heart Survey on Valvular Heart Disease", Euro Heart Journal, Mar. 2003, vol. 24, pp. 1231-1243.

McBride et al "Aortic Valve Decalcification", J Thorac Cardiovas-Surg, Jul. 1990, vol. 100, pp. 36-42.

Miller et al., "Lysis and Sonoporation of Epidermoid and Phagocytic Monolayer Cells by Diagnostic Ultrasound Activation of Contrast Agent Gas Bodies", Ultrasound in Med. & Biol., May 2007, vol. 27 (8), pp. 1107-1113.

Mohler, "Mechanisms of Aortic Valve Calcificaion", Am J Cardiol, Dec. 2004, vol. 94 (11), pp. 1396-1402.

Otto et al., "Three-Year Outcome After Balloon Aortic Valvuloplasty. Insights into Prognosis of Valvular Aortic Stenosis", Circulation, Feb. 1994, vol. 89, pp. 642-650.

Passik et al., "Temporal Changes in the Causes of Aortic Stenosis: A Surgical Pathologic Study of 646 Cases", Mayo Clin Proc, Feb. 1987, vol. 62, pp. 19-123.

Quaden et al., "Percutaneous Aortic Valve Replacement: Resection Before Implantation", Eur J Cardiothorac Surg, Jan. 2005, vol. 27, pp. 836-840.

Riebman et al., "New Concepts in the Management of Patients with Aortic Valve Disease", Abstract, Valvular Heart Disease, JACC, Mar. 2004, p. 34A.

Rosenchein et al., "Percutaneous Transluminal Therapy of Occluded Saphenous Vein Grafts" Circulation, Jan. 1999, vol. 99, pp. 26-29.

Sakata et al., "Percutaneous Balloon Aortic Valvuloplasty: Antegrade Transseptal vs. Conventional Retrograde Transarterial Approach", Catheter Cardiovasc Interv., Mar. 2005, vol. 64 (3), pp. 314-321.

Sasaki et al., "Scanning Electron Microscopy and Fourier Transformed Infrared Spectroscopy Analysis of Bone Removal Using Er:YAG and CO2 Lasers", J Periodontol., Jun. 2002, vol. 73 (6), pp. 643-652.

Search Report and Written Opinion dated Dec. 10, 2012 for PCT Application No. PCT/US2012/043636.

Search Report and Written Opinion dated Dec. 6, 2016 for PCT Application No. PCT/US2016/047831.

Search Report and Written Opinion dated Apr. 19, 2014 PCT Application No. PCT/US2012/061215.

Search Report and Written Opinion dated Apr. 19, 2014 PCT Application No. PCT/US2012/061219.

Search Report and Written Opinion dated Mar. 2, 2015 for PCT Application No. PCT/US2014/029549.

Search Report and Written Opinion dated May 1, 2012 for PCT Application No. PCT/US2011/065627.

Search Report and Written Opinion dated May 22, 2007 for PCT Application No. PCT/US2005/044543.

(56) References Cited

OTHER PUBLICATIONS

Search Report and Written Opinion dated Oct. 20, 2014 for PCT Application No. PCT/US2014/038849.
Search Report and Written Opinion dated Sep. 4, 2014 for PCT Application No. PCT/US2014/014704.
The CoreValve System Medtronic, 2012, 4 Pages.
Van Den Brand et al., "Histological Changes in the Aortic Valve after Balloon Dilation: Evidence for a Delayed Healing Process", Br Heart J, Jun. 1992,vol. 67, pp. 445-459.
Verdaadadonk et al., "The Mechanism of Action of the Ultrasonic Tissue Resectors Disclosed Using High-Speed and Thermal Imaging Techniques", SPIE, Jan. 1999, vol. 3594, pp. 221-231.
Voelker et al., "Inoperative Valvuloplasty in Calcific Aortic Stenosis: a Study Comparing the Mechanism of a Novel Expandable Device with Conventional Balloon Dilation", Am Heart J., Nov. 1991, vol. 122 (5), pp. 1327-1333.
Waller et al., "Catheter Balloon Valvuloplasty of Stenotic Aortic Valves. Part II: Balloon Valvuloplasty During Life Subsequent Tissue Examination", Clin Cardiol., Nov. 1991, vol. 14 (11), pp. 924-930.
Wang, "Balloon Aortic Valvuloplasty", Prog Cardiovasc Dis., Jul.-Aug. 1997, vol. 40 (1), pp. 27-36.
Wilson et al., "Elastography—The movement Begins", Phys. Med. Biol., Jun. 2000, vol. 45, pp. 1409-1421.
Yock et al., "Catheter-Based Ultrasound Thrombolysis", Circulation, Mar. 1997, vol. 95 (6), pp. 1411-1416.
International Search Report and Written Opinion dated Jul. 11, 2018 for PCT Application No. PCT/US2018/027990, 15 pages.
International Search Report and Written Opinion dated Jun. 28, 2018 for PCT Application No. PCT/US2018/027983, 15 pages.
International Search Report and Written Opinion dated Aug. 3, 2018 for PCT Application No. PCT/US2018035086, 15 pages.
International Search Report and Written Opinion dated Aug. 9, 2018 for PCT Application No. PCT/US2018/035081, 11 pages.
International Search Report and Written Opinion dated Jul. 3, 2018 for PCT Application No. PCT/US2018/031438, 14 pages.
International Search Report and Written Opinion dated Sep. 11, 2018 for PCT Application No. PCT/US2018/038841, 15 pages.
International Search Report and Written Opinion dated Sep. 4, 2018 for PCT Application No. PCT/US2018/027966, 17 pages.
International Search Report and Written Opinion dated Sep. 11, 2018 for PCT Application No. PCT/US2018/038847, 18 pages.
First Office Action, China National Intellectual Property Administation, Application No. 201880031007.6, dated Jun. 10, 2021.
Notice of Reasons for Rejection, Japanese Patent Application No. 2019-561301, dated Apr. 27, 2022.

* cited by examiner

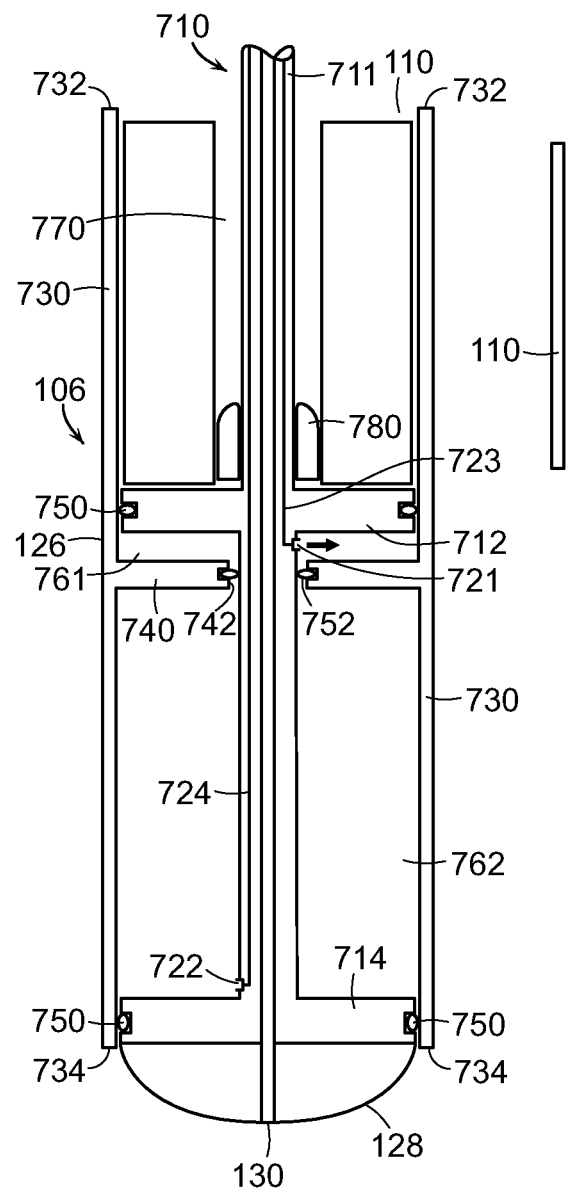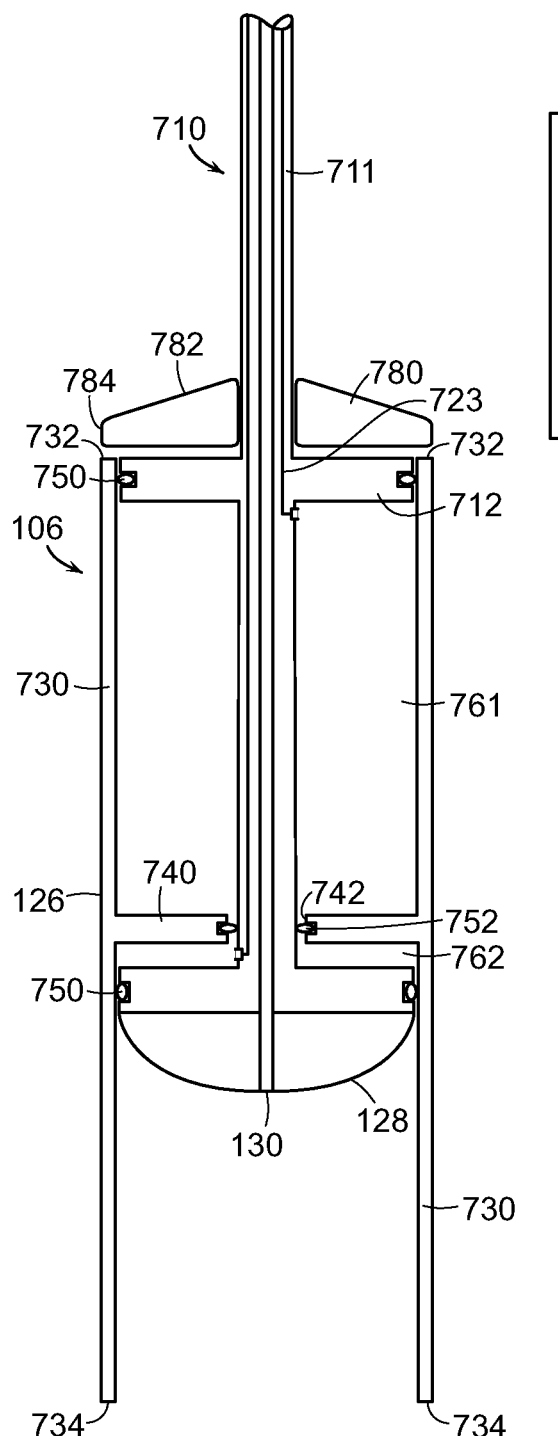
FIG. 7A
FIG. 7B

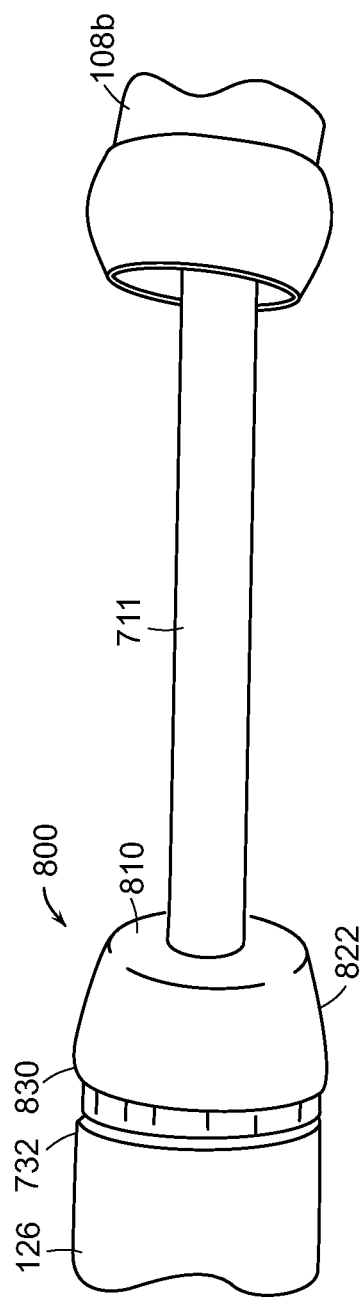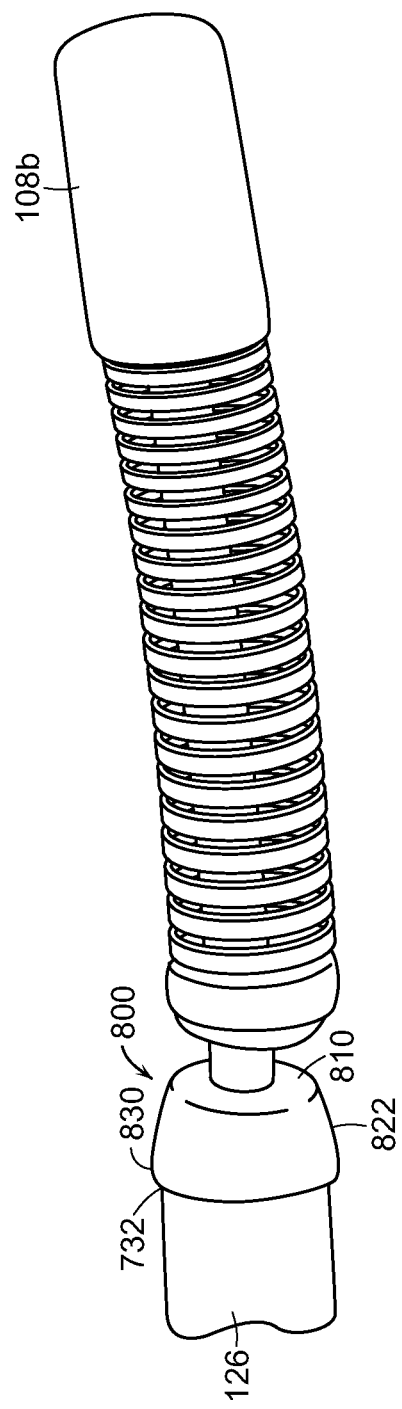

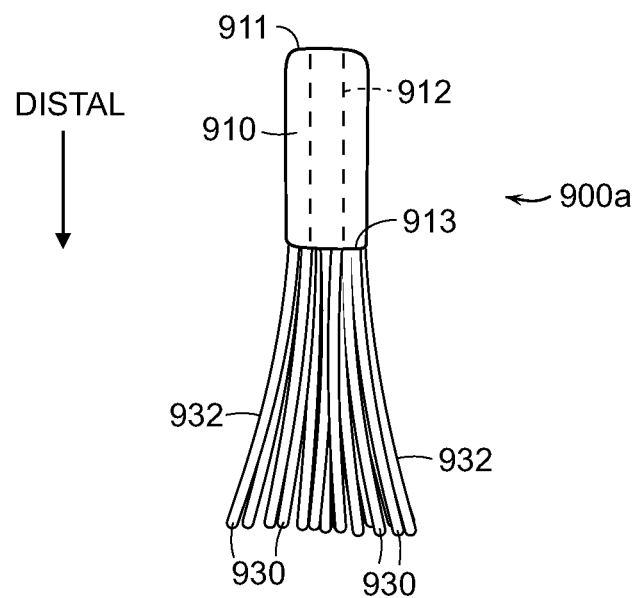
FIG. 10A
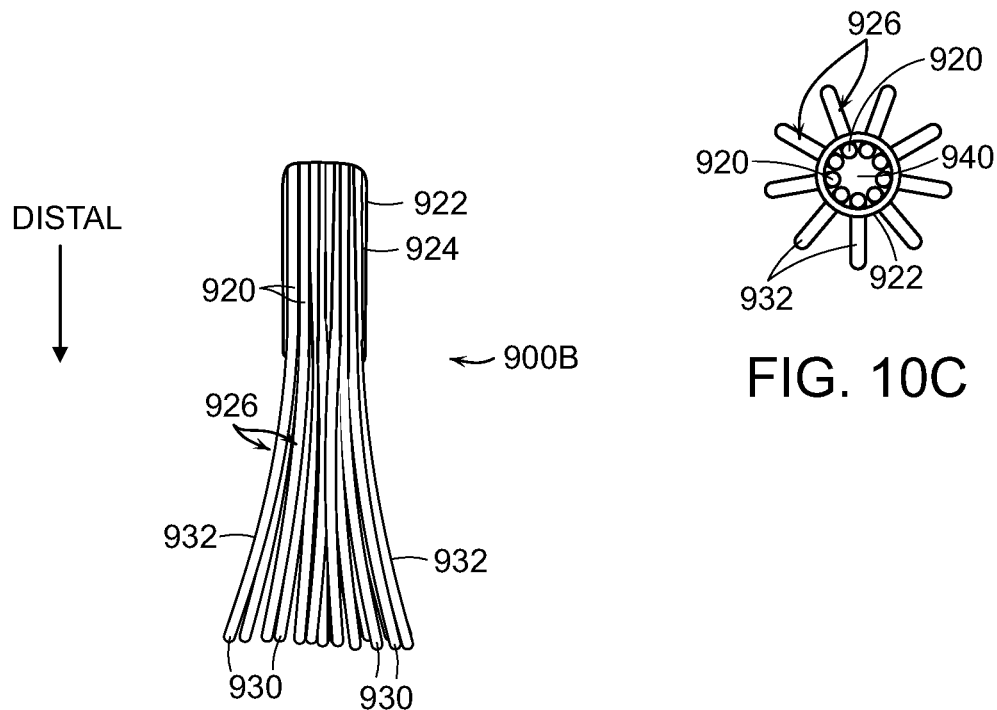
FIG. 10C
FIG. 10B

DELIVERY SYSTEMS FOR DELIVERING PROSTHETIC HEART VALVE DEVICES AND ASSOCIATED METHODS

This application is a continuation of U.S. patent application Ser. No. 15/592,507, filed May 11, 2017, the entire content of which is incorporated herein by reference.

CROSS-REFERENCE TO RELATED APPLICATIONS

The present application incorporates by reference the subject matter of the following applications in their entireties: (1) International Patent Application No. PCT/US2014/029549, filed Mar. 14, 2014; (2) International Patent Application No. PCT/US2012/061219, filed Oct. 19, 2012; (3) International Patent Application No. PCT/US2012/061215, filed Oct. 19, 2012; (4) International Patent Application No. PCT/US2012/043636, filed Jun. 21, 2012; (5) U.S. application Ser. No. 15/490,047, filed Apr. 18, 2017; (6) U.S. application Ser. No. 15/490,008, filed Apr. 18, 2017; and (7) U.S. application Ser. No. 15/490,024, filed Apr. 18, 2017.

TECHNICAL FIELD

The present technology relates generally to systems for delivering prosthetic heart valve devices. In particular, several embodiments of the present technology are related to hydraulic systems for percutaneously delivering prosthetic heart valve devices into mitral valves and associated methods.

BACKGROUND

Heart valves can be affected by several conditions. For example, mitral valves can be affected by mitral valve regurgitation, mitral valve prolapse and mitral valve stenosis. Mitral valve regurgitation is abnormal leaking of blood from the left ventricle into the left atrium caused by a disorder of the heart in which the leaflets of the mitral valve fail to coapt into apposition at peak contraction pressures. The mitral valve leaflets may not coapt sufficiently because heart diseases often cause dilation of the heart muscle, which in turn enlarges the native mitral valve annulus to the extent that the leaflets do not coapt during systole. Abnormal backflow can also occur when the papillary muscles are functionally compromised due to ischemia or other conditions. More specifically, as the left ventricle contracts during systole, the affected papillary muscles do not contract sufficiently to effect proper closure of the leaflets.

Mitral valve prolapse is a condition when the mitral leaflets bulge abnormally up into the left atrium. This can cause irregular behavior of the mitral valve and lead to mitral valve regurgitation. The leaflets may prolapse and fail to coapt because the tendons connecting the papillary muscles to the inferior side of the mitral valve leaflets (chordae tendineae) may tear or stretch. Mitral valve stenosis is a narrowing of the mitral valve orifice that impedes filling of the left ventricle in diastole.

Mitral valve regurgitation is often treated using diuretics and/or vasodilators to reduce the amount of blood flowing back into the left atrium. Surgical approaches (open and intravascular) for either the repair or replacement of the valve have also been used to treat mitral valve regurgitation. For example, typical repair techniques involve cinching or resecting portions of the dilated annulus. Cinching, for example, includes implanting annular or peri-annular rings that are generally secured to the annulus or surrounding tissue. Other repair procedures suture or clip the valve leaflets into partial apposition with one another.

Alternatively, more invasive procedures replace the entire valve itself by implanting mechanical valves or biological tissue into the heart in place of the native mitral valve. These invasive procedures conventionally require large open thoracotomies and are thus very painful, have significant morbidity, and require long recovery periods. Moreover, with many repair and replacement procedures, the durability of the devices or improper sizing of annuloplasty rings or replacement valves may cause additional problems for the patient. Repair procedures also require a highly skilled cardiac surgeon because poorly or inaccurately placed sutures may affect the success of procedures.

Less invasive approaches to aortic valve replacement have been implemented in recent years. Examples of pre-assembled, percutaneous prosthetic valves include, e.g., the CoreValve Revalving® System from Medtronic/CoreValve Inc. (Irvine, Calif., USA) and the Edwards-SAPIEN® Valve from Edwards Lifesciences (Irvine, Calif., USA). Both valve systems include an expandable frame and a tri-leaflet bio-prosthetic valve attached to the expandable frame. The aortic valve is substantially symmetric, circular, and has a muscular annulus. The expandable frames in aortic applications have a symmetric, circular shape at the aortic valve annulus to match the native anatomy, but also because tri-leaflet prosthetic valves require circular symmetry for proper coaptation of the prosthetic leaflets. Thus, aortic valve anatomy lends itself to an expandable frame housing a replacement valve since the aortic valve anatomy is substantially uniform, symmetric, and fairly muscular. Other heart valve anatomies, however, are not uniform, symmetric or sufficiently muscular, and thus transvascular aortic valve replacement devises may not be well suited for other types of heart valves.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent. The headings provided herein are for convenience only.

FIG. 7A is a partially schematic cross-sectional view of a distal portion of a system in a containment configuration in accordance with some embodiments of the present technology.

FIG. 7B is a partially schematic cross-sectional view of a distal portion of a system in a deployment configuration in accordance with some embodiments of the present technology.

FIGS. 9A and 9B are side views of the atraumatic member of FIG. 8A when the capsule is in the fully extended position (FIG. 9A) and the fully retracted position (FIG. 9B).

FIGS. 10A and 10B are side views and FIG. 10C is a top view of atraumatic members for use in delivery systems in accordance with some embodiments of the present technology.

DETAILED DESCRIPTION

Figure 1:
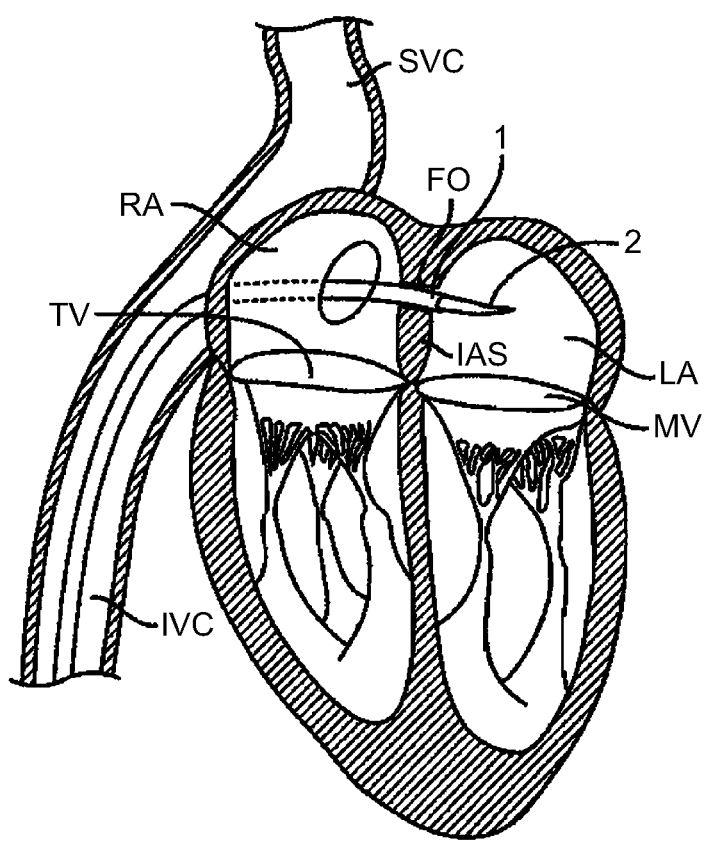
FIG. 1 is a schematic, cross-sectional illustration of the heart showing an antegrade approach to the native mitral valve from the venous vasculature in accordance with various embodiments of the present technology.

The present technology is generally directed to hydraulic systems for delivering prosthetic heart valve devices and associated methods. Specific details of several embodiments of the present technology are described herein with reference to FIGS. 1-25. Although many of the embodiments are described with respect to devices, systems, and methods for delivering prosthetic heart valve devices to a native mitral valve, other applications and other embodiments in addition to those described herein are within the scope of the present technology. For example, at least some embodiments of the present technology may be useful for delivering prosthetics to other valves, such as the tricuspid valve or the aortic valve. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein, and that these and many embodiments can be without several of the configurations, components, and/or procedures shown or described herein without deviating from the present technology.

With regard to the terms "distal" and "proximal" within this description, unless otherwise specified, the terms can reference relative positions of portions of a prosthetic valve device and/or an associated delivery device with reference to an operator and/or a location in the vasculature or heart. For example, in referring to a delivery catheter suitable to deliver and position various prosthetic valve devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a prosthetic heart valve device, the terms "proximal" and "distal" can refer to the location of portions of the device with respect to the direction of blood flow. For example, proximal can refer to an upstream position or a location where blood flows into the device (e.g., inflow region), and distal can refer to a downstream position or a location where blood flows out of the device (e.g., outflow region).

Overview

Several embodiments of the present technology are directed to delivery systems and mitral valve replacement devices that address the unique challenges of percutaneously replacing native mitral valves. The delivery systems and implantable devices are well-suited to be recaptured in a percutaneous delivery device after being partially deployed for repositioning or removing the device. The delivery systems are also well-suited for deploying self-expanding prosthetic heart valve replacement devices and withdrawing the delivery systems from the patient. Compared to replacing aortic valves, percutaneous mitral valve replacement faces unique anatomical obstacles that render percutaneous mitral valve replacement significantly more challenging than aortic valve replacement. First, unlike relatively symmetric and uniform aortic valves, the mitral valve annulus has a non-circular D-shape or kidney-like shape, with a non-planar, saddle-like geometry often lacking symmetry. The complex and highly variable anatomy of mitral valves makes it difficult to design a mitral valve prosthesis that conforms well to the native mitral annulus of specific patients. As a result, the prosthesis may not fit well with the native leaflets and/or annulus, which can leave gaps that allows backflow of blood to occur. For example, placement of a cylindrical valve prosthesis in a native mitral valve may leave gaps in commissural regions of the native valve through which perivalvular leaks may occur.

Current prosthetic valves developed for percutaneous aortic valve replacement are unsuitable for use in mitral valves. First, many of these devices require a direct, structural connection between the stent-like structure that contacts the annulus and/or leaflets and the prosthetic valve. In several devices, the stent posts which support the prosthetic valve also contact the annulus or other surrounding tissue.

These types of devices directly transfer the forces exerted by the tissue and blood as the heart contracts to the valve support and the prosthetic leaflets, which in turn distorts the valve support from its desired cylindrical shape. This is a concern because most cardiac replacement devices use tri-leaflet valves, which require a substantially symmetric, cylindrical support around the prosthetic valve for proper opening and closing of the three leaflets over years of life. As a result, when these devices are subject to movement and forces from the annulus and other surrounding tissues, the prostheses may be compressed and/or distorted causing the prosthetic leaflets to malfunction. Moreover, a diseased mitral annulus is much larger than any available prosthetic aortic valve. As the size of the valve increases, the forces on the valve leaflets increase dramatically, so simply increasing the size of an aortic prosthesis to the size of a dilated mitral valve annulus would require dramatically thicker, taller leaflets, and might not be feasible.

In addition to its irregular, complex shape, which changes size over the course of each heartbeat, the mitral valve annulus lacks a significant amount of radial support from surrounding tissue. Compared to aortic valves, which are completely surrounded by fibro-elastic tissue that provides sufficient support for anchoring a prosthetic valve, mitral valves are bound by muscular tissue on the outer wall only. The inner wall of the mitral valve anatomy is bound by a thin vessel wall separating the mitral valve annulus from the inferior portion of the aortic outflow tract. As a result, significant radial forces on the mitral annulus, such as those imparted by an expanding stent prosthesis, could lead to collapse of the inferior portion of the aortic tract. Moreover, larger prostheses exert more force and expand to larger dimensions, which exacerbates this problem for mitral valve replacement applications.

The chordae tendineae of the left ventricle may also present an obstacle in deploying a mitral valve prosthesis. Unlike aortic valves, mitral valves have a maze of cordage under the leaflets in the left ventricle that restrict the movement and position of a deployment catheter and the replacement device during implantation. As a result, deploying, positioning and anchoring a valve replacement device on the ventricular side of the native mitral valve annulus is complicated.

The present technology provides systems, methods and apparatus to treat heart valves of the body, such as the mitral valve, that address the challenges associated with the anatomy of the mitral valve. The present technology provides for repositioning and/or removal of a partially deployed device, and/or for atraumatic removal of the delivery system from the patient. The apparatus and methods enable a percutaneous approach using a catheter delivered intravascularly through a vein or artery into the heart, or through a cannula inserted through the heart wall. For example, the apparatus and methods are particularly well-suited for trans-septal and trans-apical approaches, but can also be trans-atrial and direct aortic delivery of a prosthetic replacement valve to a target location in the heart. Additionally, several embodiments of the devices and methods as described herein can be combined with many known surgeries and procedures, such as known methods of accessing the valves of the heart (e.g., the mitral valve or triscuspid valve) with antegrade or retrograde approaches, and combinations thereof.

The systems and methods described herein facilitate controlled delivery of a prosthetic heart valve device using trans-apical or trans-septal delivery approaches, allow resheathing of the prosthetic heart valve device after partial deployment of the device to reposition and/or remove the device, and/or provide for atraumatic removal of the delivery systems from the patient. Systems in accordance with several embodiments of the present technology comprise an elongated catheter body, a delivery capsule carried by the catheter body, and an expandable atraumatic member. The delivery capsule includes a platform and a housing having a sidewall and a proximal rim, and the capsule is configured to releasably contain a prosthetic heart valve device. The housing is configured to slide along the platform from a containment configuration to a deployment configuration. The expandable atraumatic member is carried by the capsule (e.g., in the capsule), and the atraumatic member has an opening through which a portion of a support member extends, an atraumatic surface, and a peripheral portion. In some embodiments, the atraumatic member has (a) a compacted configuration in which the atraumatic member is configured to be located within at least a portion of an implantable device while constrained with the capsule, and (b) an expanded configuration in which the peripheral portion extends laterally outward beyond the proximal rim of the housing (e.g., radially outward of the diameter of the proximal rim). In the expanded configuration, the implantable device is spaced apart from the atraumatic member, and the atraumatic member is configured to protect tissue of the heart and the vasculature from potentially being damaged by the proximal rim of the housing as the delivery system is withdrawn in a proximal direction through the patient. Additionally, the atraumatic member can expand outwardly against the implantable device during deployment to assist in disengaging the implantable device from the capsule.

Access to the Mitral Valve

To better understand the structure and operation of valve replacement devices in accordance with the present technology, it is helpful to first understand approaches for implanting the devices. The mitral valve or other type of atrioventricular valve can be accessed through the patient's vasculature in a percutaneous manner. By percutaneous it is meant that a location of the vasculature remote from the heart is accessed through the skin, typically using a surgical cut down procedure or a minimally invasive procedure, such as using needle access through, for example, the Seldinger technique. The ability to percutaneously access the remote vasculature is well known and described in the patent and medical literature. Depending on the point of vascular access, access to the mitral valve may be antegrade and may rely on entry into the left atrium by crossing the inter-atrial septum (e.g., a trans-septal approach). Alternatively, access to the mitral valve can be retrograde where the left ventricle is entered through the aortic valve. Access to the mitral valve may also be achieved using a cannula via a trans-apical approach. Depending on the approach, the interventional tools and supporting catheter(s) may be advanced to the heart intravascularly and positioned adjacent the target cardiac valve in a variety of manners, as described herein.

FIG. 1 illustrates a stage of a trans-septal approach for implanting a valve replacement device. In a trans-septal approach, access is via the inferior vena cava IVC or superior vena cava SVC, through the right atrium RA, across the inter-atrial septum IAS, and into the left atrium LA above the mitral valve MV. As shown in FIG. 1, a catheter 1 having a needle 2 moves from the inferior vena cava IVC into the right atrium RA. Once the catheter 1 reaches the anterior side of the inter-atrial septum IAS, the needle 2 advances so that it penetrates through the septum, for example at the fossa ovalis FO or the foramen ovale into the left atrium LA. At this point, a guidewire replaces the needle 2 and the catheter 1 is withdrawn.

Figure 2:
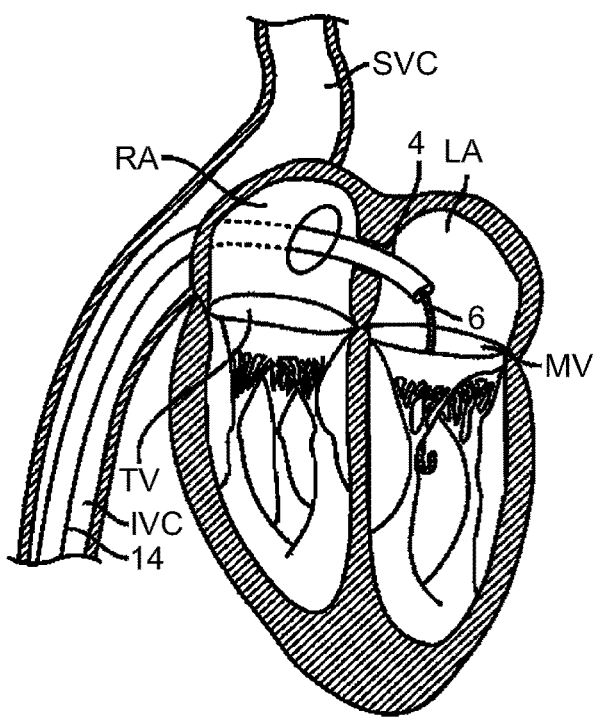
FIG. 2 is a schematic, cross-sectional illustration of the heart showing access through the inter-atrial septum (IAS) maintained by the placement of a guide catheter over a guidewire in accordance with various embodiments of the present technology.

FIG. 2 illustrates a subsequent stage of a trans-septal approach in which guidewire 6 and guide catheter 4 pass through the inter-atrial septum IAS. The guide catheter 4 provides access to the mitral valve for implanting a valve replacement device in accordance with the technology.

In an alternative antegrade approach (not shown), surgical access may be obtained through an intercostal incision, preferably without removing ribs, and a small puncture or incision may be made in the left atrial wall. A guide catheter passes through this puncture or incision directly into the left atrium, sealed by a purse string-suture.

The antegrade or trans-septal approach to the mitral valve, as described above, can be advantageous in many respects. For example, antegrade approaches will usually enable more precise and effective centering and stabilization of the guide catheter and/or prosthetic valve device. The antegrade approach may also reduce the risk of damaging the chordae tendineae or other subvalvular structures with a catheter or other interventional tool. Additionally, the antegrade approach may decrease risks associated with crossing the aortic valve as in retrograde approaches. This can be particularly relevant to patients with prosthetic aortic valves, which cannot be crossed at all or without substantial risk of damage.

Figure 3:
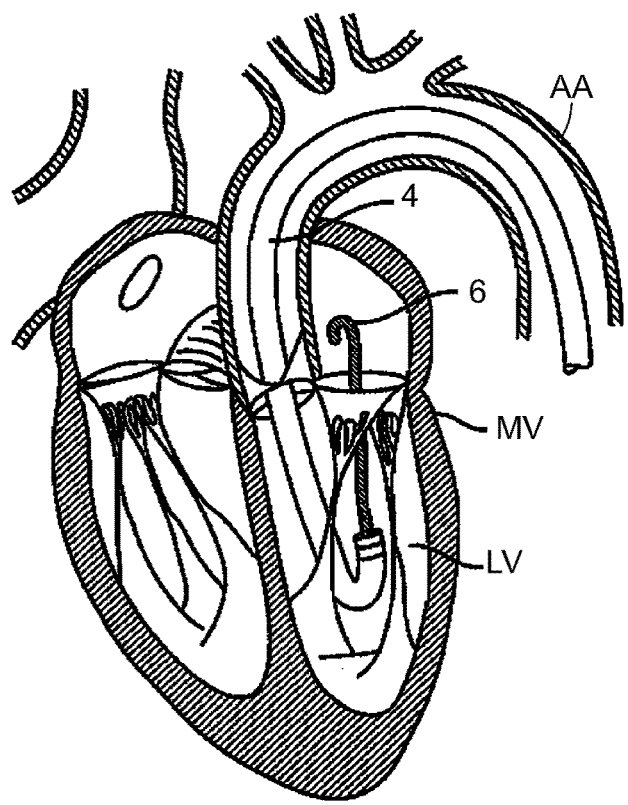
FIGS. 3 and 4 are schematic, cross-sectional illustrations of the heart showing retrograde approaches to the native mitral valve through the aortic valve and arterial vasculature in accordance with various embodiments of the present technology.
Figure 4:
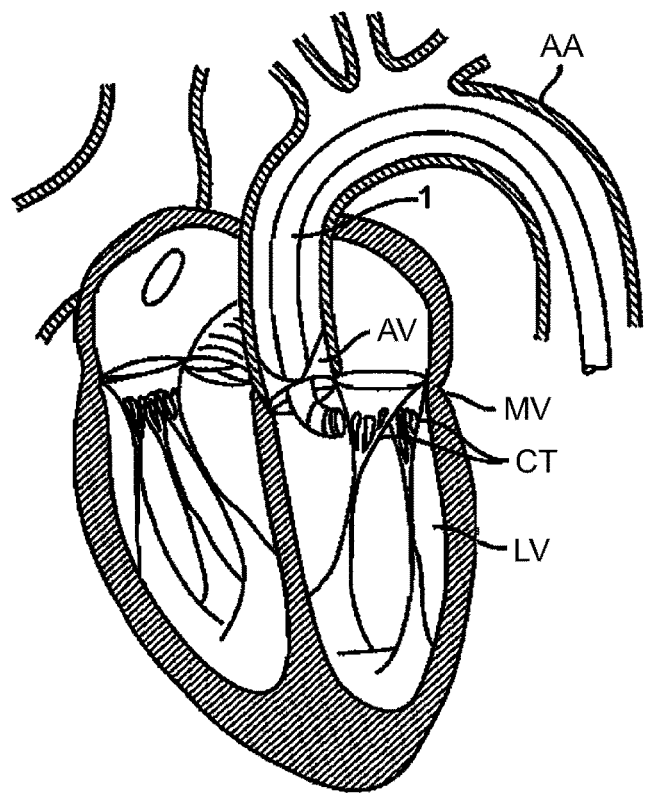

FIGS. 3 and 4 show examples of a retrograde approaches to access the mitral valve. Access to the mitral valve MV may be achieved from the aortic arch AA, across the aortic valve AV, and into the left ventricle LV below the mitral valve MV. The aortic arch AA may be accessed through a conventional femoral artery access route or through more direct approaches via the brachial artery, axillary artery, radial artery, or carotid artery. Such access may be achieved with the use of a guidewire 6. Once in place, a guide catheter 4 may be tracked over the guidewire 6. Alternatively, a surgical approach may be taken through an incision in the chest, preferably intercostally without removing ribs, and placing a guide catheter through a puncture in the aorta itself. The guide catheter 4 affords subsequent access to permit placement of the prosthetic valve device, as described in more detail herein. Retrograde approaches advantageously do not need a trans-septal puncture. Cardiologists also more commonly use retrograde approaches, and thus retrograde approaches are more familiar.

Figure 5:
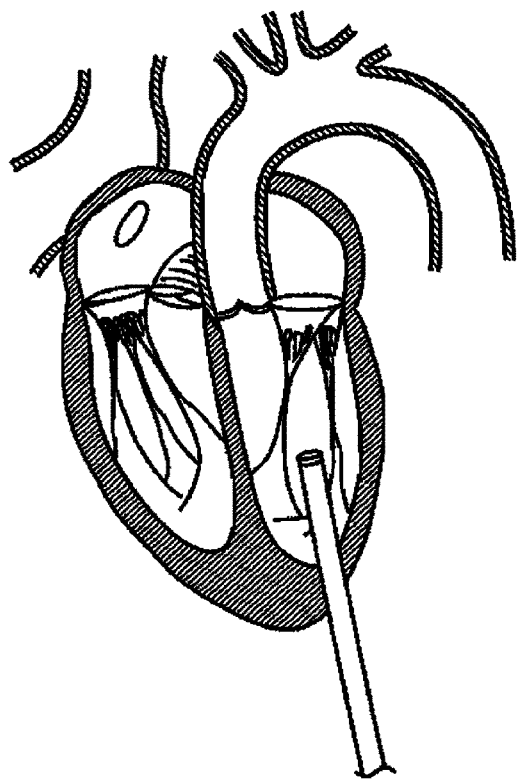
FIG. 5 is a schematic, cross-sectional illustration of the heart showing an approach to the native mitral valve using a trans-apical puncture in accordance with various embodiments of the present technology.

FIG. 5 shows a trans-apical approach via a trans-apical puncture. In this approach, access to the heart is via a thoracic incision, which can be a conventional open thoracotomy or sternotomy, or a smaller intercostal or subxyphoid incision or puncture. An access cannula is then placed through a puncture in the wall of the left ventricle at or near the apex of the heart. The catheters and prosthetic devices of the invention may then be introduced into the left ventricle through this access cannula. The trans-apical approach provides a shorter, straighter, and more direct path to the mitral or aortic valve. Further, because it does not involve intravascular access, the trans-apical approach does not require training in interventional cardiology to perform the catheterizations required in other percutaneous approaches.

Selected Embodiments of Delivery Systems for Prosthetic Heart Valve Devices

Figure 6:
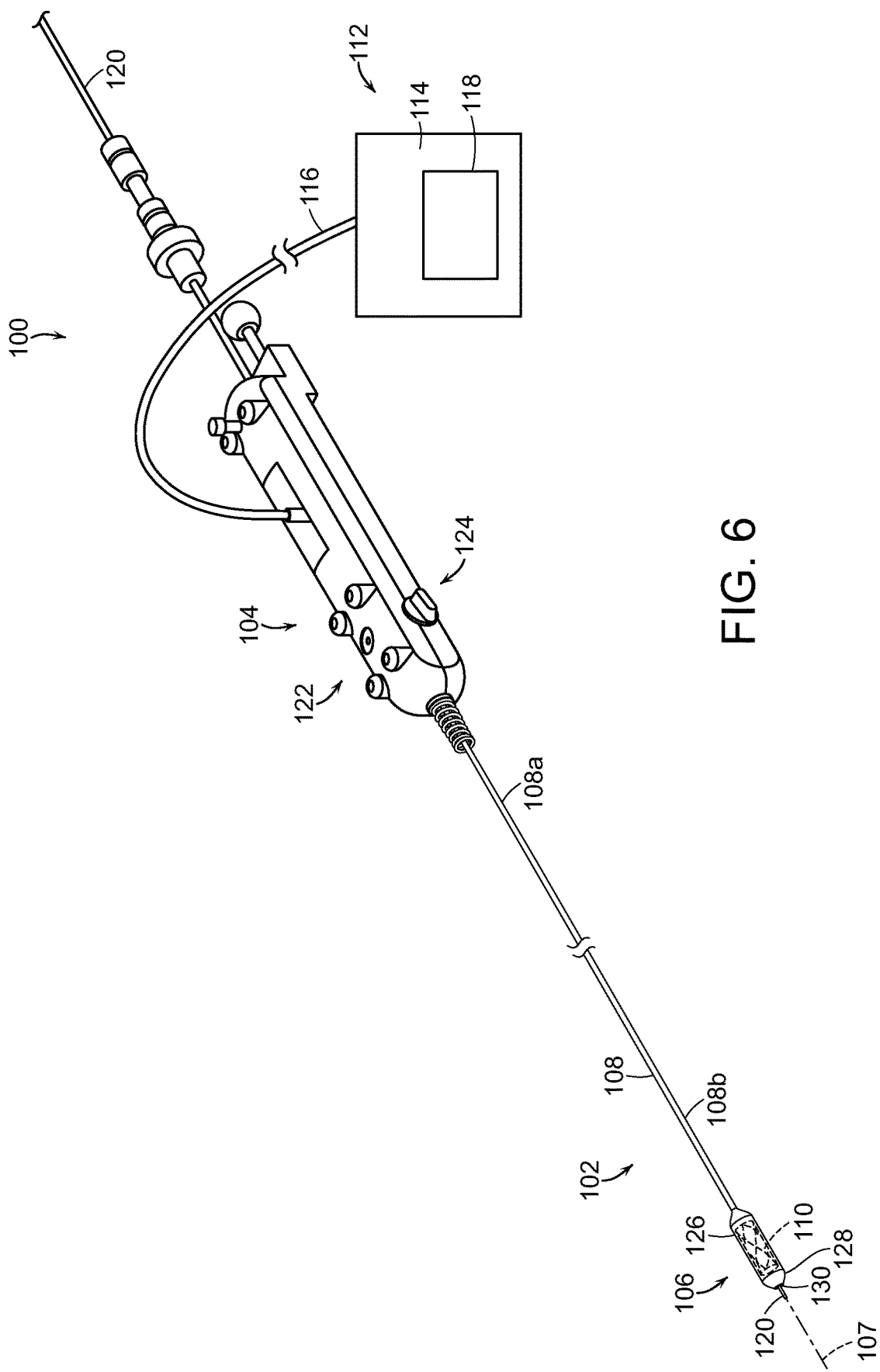
FIG. 6 is an isometric view of a system for delivering a prosthetic heart valve device configured in accordance with some embodiments of the present technology.

FIG. 6 is an isometric view of a hydraulic system 100 ("system 100") for delivering a prosthetic heart valve device configured in accordance with at least some embodiments of the present technology. The system 100 includes a catheter 102 having an elongated catheter body 108 ("catheter body 108") and a delivery capsule 106. The catheter body 108 can include a proximal portion 108a coupled to a handheld control unit 104 ("control unit 104") and a distal portion 108b carrying the delivery capsule 106. The delivery capsule 106 can be configured to contain a prosthetic heart valve device 110 (shown schematically in broken lines). The control unit 104 can provide steering capability (e.g., 360 degree rotation of the delivery capsule 106, 180 degree rotation of the delivery capsule 106, 3-axis steering, 2-axis steering, etc.) used to deliver the delivery capsule 106 to a target site (e.g., to a native mitral valve) and deploy the prosthetic heart valve device 110 at the target site. The catheter 102 can be configured to travel over a guidewire 120, which can be used to guide the delivery capsule 106 into the native heart valve. The system 100 can also include a fluid assembly 112 configured to supply fluid to and receive fluid from the catheter 102 for hydraulically moving the delivery capsule 106 to deploy the prosthetic heart valve device 110.

The fluid assembly 112 includes a fluid source 114 and a fluid line 116 fluidically coupling the fluid source 114 to the catheter 102. The fluid source 114 may contain a flowable substance (e.g., water, saline, etc.) in one or more reservoirs. The fluid line 116 can include one or more hoses, tubes, or other components (e.g., connectors, valves, etc.) through which the flowable substance can pass from the fluid source 114 to the catheter 102 and/or through which the flowable substance can drain from the catheter 102 to the fluid source 114. In other embodiments, the fluid line 116 can deliver the flowable substance to the catheter 102 from a first reservoir of the fluid source 114 and drain the flowable substance from the catheter 102 to a separate reservoir. The fluid assembly 112 can also include one or more pressurization devices (e.g., a pump), fluid connectors, fittings, valves, and/or other fluidic components that facilitate moving the fluid to and/or from the fluid source 114. As explained in further detail below, the movement of the flowable substance to and from the fluid assembly 112 can be used to deploy the prosthetic heart valve device 110 from the delivery capsule 106 and/or resheathe the prosthetic heart valve device 110 after at least partial deployment.

In certain embodiments, the fluid assembly 112 may comprise a controller 118 that controls the movement of fluid to and from the catheter 102. The controller 118 can include, without limitation, one or more computers, central processing units, processing devices, microprocessors, digital signal processors (DSPs), and/or application-specific integrated circuits (ASICs). To store information, for example, the controller 118 can include one or more storage elements, such as volatile memory, non-volatile memory, read-only memory (ROM), and/or random-access memory (RAM). The stored information can include, pumping programs, patient information, and/or other executable programs. The controller 118 can further include a manual input device (e.g., a keyboard, a touch screen, etc.) and/or an automated input device (e.g., a computer, a data storage device, servers, network, etc.). In still other embodiments, the controller 118 may include different features and/or have a different arrangement for controlling the flow of fluid into and out of the fluid source 114.

The control unit 104 can include a control assembly 122 and a steering mechanism 124. For example, the control assembly 122 can include rotational elements, such as a knob, that can be rotated to rotate the delivery capsule 106 about its longitudinal axis 107. The control assembly 122 can also include features that allow a clinician to control the hydraulic deployment mechanisms of the delivery capsule 106 and/or the fluid assembly 112. For example, the control assembly 122 can include buttons, levers, and/or other actuators that initiate unsheathing and/or resheathing the prosthetic heart valve device 110. The steering mechanism 124 can be used to steer the catheter 102 through the anatomy by bending the distal portion 108b of the catheter body 108 about a transverse axis. In other embodiments, the control unit 104 may include additional and/or different features that facilitate delivering the prosthetic heart valve device 110 to the target site.

The delivery capsule 106 includes a housing 126 configured to carry the prosthetic heart valve device 110 in the containment configuration and, optionally, an end cap 128. The end cap 128 can have an opening 130 at its distal end through which the guidewire 120 can be threaded to allow for guidewire delivery to the target site. As shown in FIG. 6, the end cap 128 can also have an atraumatic shape (e.g., a partially spherical shape, a frusto-conical shape, blunt configuration, rounded configuration, etc.) to facilitate atraumatic delivery of the delivery capsule 106 to the target site. In certain embodiments, the end cap 128 can also house a portion of the prosthetic heart valve device 110. The housing 126 and/or the end cap 128 can be made of metal, polymers, plastic, composites, combinations thereof, or other materials capable of holding the prosthetic heart valve device 110. The delivery capsule 106 is hydraulically driven via the control unit 104 and/or the fluid assembly 112 between a containment configuration for holding the prosthetic heart valve device 110 and a deployment configuration for at least partially deploying the prosthetic heart valve device 110 at the target site. The delivery capsule 106 also allows for resheathing of the prosthetic heart valve device 110 after it has been partially deployed.

FIG. 7A is a cross-sectional view of at least some embodiments of the capsule 106 in a containment configuration, and FIG. 7B is a cross-sectional view of the capsule 106 in a deployment configuration. The capsule 106 can be actuated hydraulically and capable of resheathing the device 110 to either reposition or remove the device 110 from a patient after being partially deployed. In several embodiments, the capsule 106 includes a support 710 within the housing 126. The support 710 can have a central member 711, a platform 712 extending radially outward from a medial portion of the central member 711, and an end plate 714 extending radially outward from an end portion of the central member 711. The central member 711 can be an extension of the catheter 102 or a separate component attached to the distal end 108b of the catheter body 108. The platform 712 and the end plate 714 can be shoulders or flanges having a disk-like shape or other suitable shapes. The support 710 can further include a first orifice 721, a first fluid line 723 coupled to the first orifice 721, a second orifice 722, and a second fluid line 724 coupled to the second orifice 722.

The housing 126 of the capsule 106 in this embodiment includes a side wall 730 having a proximal rim 732 and a distal terminus 734. The sidewall 730 is size to be slightly larger than the outer perimeter of the platform 712 and the end plate 714 such that seals 750 (e.g., O-rings) can fluidically seal against the inner surface of the sidewall 730. The housing 126 can further include a flange 740 extending radially inwardly from the sidewall 730, and the flange 740 can have an opening 742 through which the central member 711 of the support 710 passes. The flange 740 is configured to carry a seal 752 (e.g., an O-ring) that seals against the central member 711 of the support 710. The capsule 106 of this embodiment is configured to have a first fluid chamber 761 between the platform 712 and the flange 740, and a second fluid chamber 762 between the flange 740 and the end plate 714. The first fluid chamber 761 is open to the first orifice 721, and a second fluid chamber 762 is open to the second orifice 722. The upper portion of the sidewall 730 shown in FIG. 7A defines a chamber 770 in the containment configuration in which the prosthetic heart valve device 110 (shown schematically as an annular box) is retained during delivery to a target site.

In operation, the housing 126 of the capsule 106 moves between the containment and deployment configurations by delivering or draining a flowable substance (e.g., water, saline, etc.) to or from the first and second fluid chambers 761 and 762 via the first and second orifices 721 and 722, respectively. For example, the housing 126 moves from the containment configuration (FIG. 7A) to the deployment configuration (FIG. 7B) by delivering the flowable substance to the first fluid chamber 761 via the first orifice 721 while draining the flowable substance from the second fluid chamber 762 via the second orifice 722. Conversely, the housing moves from the deployment configuration (FIG. 7B) to the containment configuration (FIG. 7A) by delivering the flowable substance to the second fluid chamber 762 via the second orifice 722 while draining the flowable substance from the first fluid chamber 761 via the first orifice 721.

The system 100 can further include an expandable atraumatic member 780 ("atraumatic member 780") carried by the capsule 106. As best shown in FIG. 7B, the atraumatic member 780 can include an atraumatic surface 782 and a peripheral portion 784. The atraumatic member 780 is configured to be retained within the capsule 106 in the containment configuration (FIG. 7A) and expand radially outward in the deployment configuration (FIG. 7B) such that at least a peripheral portion of the atraumatic member 780 extends over at least a portion of the proximal rim 732 of the capsule 106 (e.g., radially beyond the diameter of the proximal rim 732). Referring to FIG. 7A, at least some embodiments of the atraumatic member 780 can be compacted and positioned between a distal portion of the device 110 and the central member 711 of the support 710 such that the atraumatic member 780 can, if necessary, drive the distal portion of the device 110 outward to disengage the device 110 from the platform 712. In many embodiments, the atraumatic member 780 does not need be positioned between the device 110 and the central member 711 of the support 710, but rather the atraumatic member 780 can be located distal of the distal-most portion of the device 110.

In the deployment configuration shown in FIG. 7B, the proximal rim 732 of the housing 126 is positioned distally beyond the distal-most portions of the device 110 and the atraumatic member 780. The device 110 accordingly expands radially outward beyond the housing 126, and the atraumatic member 780 expands such that at least the peripheral portion 784 of the atraumatic member 780 is laterally (e.g., radially) outward with respect to the proximal rim 732 of the housing 126. For example, the atraumatic member 780 covers the proximal rim 732 in a proximal direction. The atraumatic member 780 accordingly protects tissue of the heart and vasculature as the catheter 102 is withdrawn proximally to remove the delivery device after deploying the device 110.

Figure 8A:
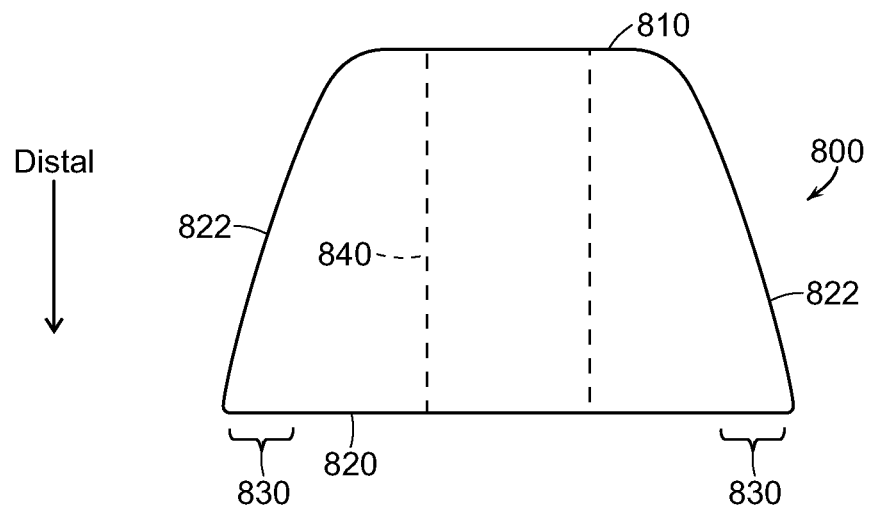
FIG. 8A is a side view of an atraumatic member for use in a delivery system in accordance with some embodiments of the present technology.

Several embodiments of the atraumatic member 780 are shown in FIGS. 8A-11. FIG. 8A is an isometric view an expandable atraumatic member 800 ("atraumatic member 800") comprising a truncated conical member having a proximal surface 810, a distal surface 820, an atraumatic surface 822 between the proximal surface 810 and the distal surface 820, and a peripheral region 830. At least a portion of the atraumatic surface 822 can slope outwardly in the distal direction. The atraumatic surface 822, for example, inclines (e.g., flares) outwardly with increasing distance distally. As a result, the atraumatic surface 800 directs the capsule 106 through openings and the lumens of the vasculature as the catheter 102 (FIG. 1) is withdrawn from the patient. The peripheral portion 830 of the atraumatic member 800 is configured to cover the proximal rim 732 of the housing 126 (FIG. 7B) and thereby prevent the proximal rim 732 from damaging the tissue as the catheter 102 is withdrawn. The atraumatic member 800 further includes an opening 840 configured to receive the central member 711 of the support 710.

The atraumatic member 800 can be a polymeric material, a braided material, or a structure formed from individual struts. In the case of a polymeric material, the atraumatic member 800 can be a porous material, such as an open cell foam or closed cell foam. Other polymeric materials that expand when unconstrained, such as Silicone, can also be used. The atraumatic member 800 can alternatively be a cage other structure formed from struts or a braid of shape-memory wires or other types of wires that have a truncated conical shape in a fully expanded unbiased state. The wires of the braid can comprise one or more of nitinol, stainless steel, drawn filled tubes (e.g., nitinol and platinum), and cobalt-chromium alloy.

Figure 8B:
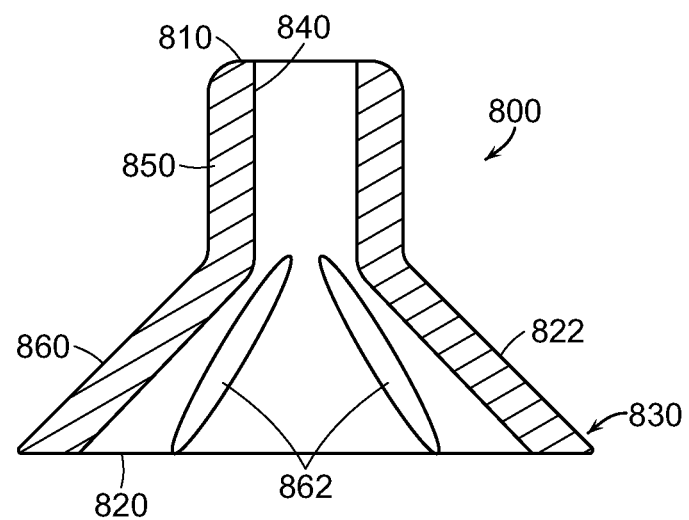
FIG. 8B is a side cross-sectional view of an atraumatic member for use in a delivery system in accordance with some embodiments of the present technology.

FIG. 8B is a side cross-sectional view of some embodiments of the atraumatic member 800 that further include a hub 850 and a disc 860 extending distally and radially outward from the hub 850 in an unconstrained state. The atraumatic member 800 shown in FIG. 8B can be made from Silicone or some other suitable polymeric material, and the hub 850 and the disc 860 can be formed integrally with each other. For example, the hub 850 and the disc 860 can be molded or three-dimensionally printed from Silicone or another suitable material. The opening 840 can extend through the hub 850. The disc 860 can flex inwardly at the hub 850 to be loaded into a delivery capsule and then self-expand radially outwardly with respect to the hub when unconstrained (i.e., released from the delivery capsule). The atraumatic member 800 shown in FIG. 8B can further include supports 862 (e.g., arms) on the inner surface of the disc 860. The supports 862 can be formed integrally with the disc 860, such as by molding or three-dimensional printing, or the supports 862 can be separate components (e.g., metal rods) attached to or molded within the disc 860.

FIGS. 9A and 9B are side views of some embodiments of the atraumatic member 800 and the housing 126 of the capsule 106 when the housing 126 is in different positions. FIG. 9A, more specifically, shows the atraumatic member 800 when the housing 126 is in the fully extended position of FIG. 7B after the implantable device and the atraumatic member 800 have fully expanded. At this stage, the peripheral portion 830 of the atraumatic member 800 extends outwardly beyond the radius of the proximal rim 732 of the housing 126. FIG. 9B shows the system after the housing 126 has been retracted to its original position shown in FIG. 7A causing the atraumatic member 800 to slide proximally along the central member 711 (FIG. 9A) of the support. At this stage, the peripheral portion 830 of the atraumatic member 800 remains over the proximal rim 732 of the housing 126 to protect tissue of the heart and vasculature of the patient as the delivery system is withdrawn.

FIG. 10A is a side view illustrating an atraumatic member 900a in accordance with several embodiments of the present technology. The atraumatic member 900a has hub 910 with a proximal surface 911, an opening 912 to receive the central member 711 of the support 710, and a distal end 913. The hub 910 can be a short tubular member. The atraumatic member 900a further includes a plurality of arms 930 extending distally from the distal end 913 of the hub 910. FIG. 10A shows the atraumatic member 900a in an expanded state in which the arms 930 flare radially outwardly in the distal direction. In this embodiment, the arms 930 have a semi-hyperboloid shape. The arms 930 have outer surfaces 932 that together define the atraumatic surface of the atraumatic member 900a.

FIG. 10B is a side view and FIG. 10C is a top view illustrating an atraumatic member 900b in accordance with several embodiments of the present technology. The atraumatic member 900b is formed from a cut hypo-tube having a plurality of first sections 920 held together by a casing 922 to form a proximal hub 924 (FIG. 10B) and a plurality of second sections 926 that extends distally from the proximal hub 924 to define a plurality of arms 930 (FIG. 10B). The first sections 926 can be arranged to form an opening 940 (FIG. 10C) configured to receive the central member 711 (FIG. 7A) of the support 710 (FIG. 7A). As with the atraumatic member 900a shown in FIG. 10A, the arms 930 of the atraumatic member 900b flare radially outwardly in the distal direction when the atraumatic member 900b is in the expanded state. Both of the atraumatic members 900a and 900b can be formed from a shape memory material, such as nitinol, or other materials (e.g., stainless steel or polymeric materials). Additionally, the arms 930 of both of the atraumatic members 900a and 900b have outer surfaces 932 that together define an atraumatic surface.

Figure 11:
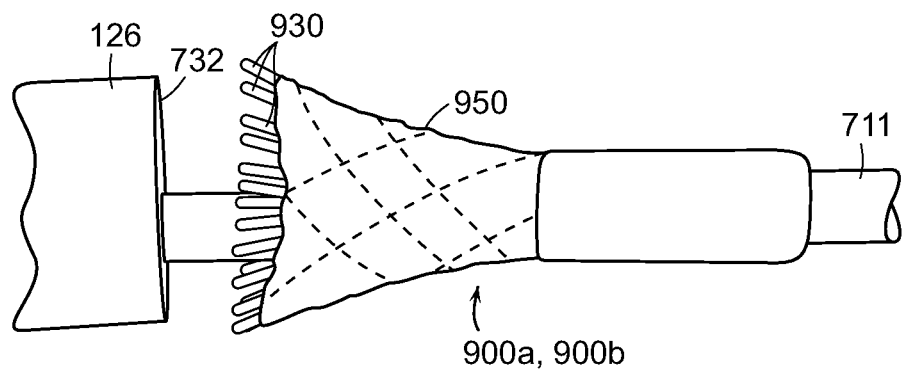
FIG. 11 is a side view of the atraumatic members of FIGS. 10A-10C after the atraumatic member has expanded.

FIG. 11 is a side view illustrating the atraumatic members 900a or 900b mounted to the central member 711 in an expanded state in which the arms 930 extend radially outwardly such that the distal peripheral portions of the arms 930 are radially outward of the proximal rim 732 of the housing 126. The distal portions of the arms 930 accordingly define a peripheral portion of the atraumatic members 900a or 900b that extend laterally (e.g., radially) outward of the proximal rim 732 to cover the proximal rim 732 of the housing 126 in the proximally facing direction. In operation, the arms 930 of either of the atraumatic members 900a and 900b sufficiently cover the proximal rim 732 of the housing 126 in the proximally facing direction to protect the tissue of the heart and/or the vasculature of the patient as the catheter 102 is withdrawn. Additionally, the radial expansion of the arms 930 can assist in disengaging an implantable device from the capsule by pushing radially outward against a distal portion of the implantable device.

Additional embodiments of the atraumatic members 900a and 900b can optionally include a covering 950 (FIG. 11) over the arms 930. For example, a fabric covering made from Dacron®, a braided wire mesh, or another suitable material can be placed over the outer surface of the arms 930 and/or line the inner surface of the arms 930 to further enhance the protective nature of the arms 930. In alternative embodiments, instead of separate arms 930, the atraumatic members 900a and 900b can have a fluted skirt made from a fabric, braided mesh of metal wires, or a thin sheet of metal that self-expands radially outwardly when not constricted by the housing 126 of the capsule 106.

In addition to protecting heart and vasculature tissue, atraumatic members of the present technology enable the housing 126 to have an open proximal end. Referring to FIG.

7A, for example, the capsule 106 does not need a proximal cap that seals to or otherwise covers the proximal rim 732 in the containment configuration. This reduces the length of the capsule 106, which is desirable to enable the capsule 106 to pass through turns and corners of the vasculature.

Selected Embodiments of Prosthetic Heart Valve Devices

The delivery systems with atraumatic member described above with reference to FIGS. 6-11 can be configured to deliver various prosthetic heart valve devices, such as prosthetic valve devices for replacement of the mitral valve and/or other valves (e.g., a bicuspid or tricuspid valve) in the heart of the patient. Examples of these prosthetic heart valve devices, system components, and associated methods are described in this section with reference to FIGS. 12A-25. Specific elements, substructures, advantages, uses, and/or other features of the embodiments described with reference to FIGS. 12A-25 can be suitably interchanged, substituted or otherwise configured with one another. Furthermore, suitable elements of the embodiments described with reference to FIGS. 12A-25 can be used as stand-alone and/or self-contained devices.

Figure 12A:
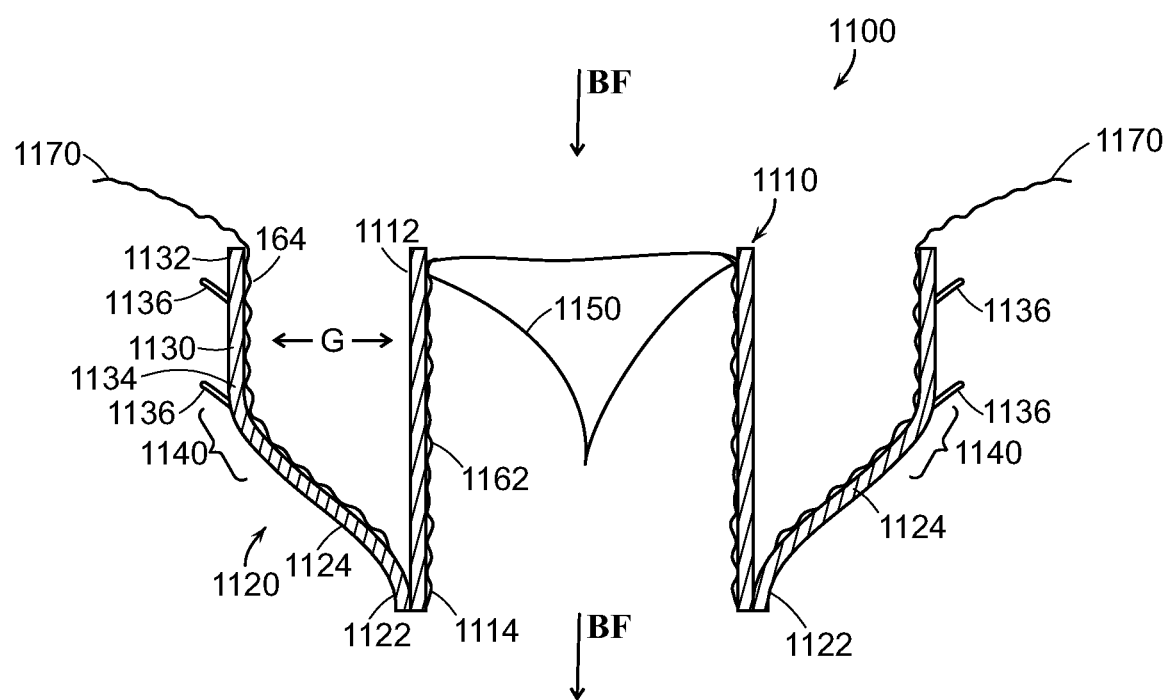
FIG. 12A is a cross-sectional side view and FIG. 12B is a top view schematically illustrating a prosthetic heart valve device in accordance with some embodiments of the present technology.
Figure 12B:
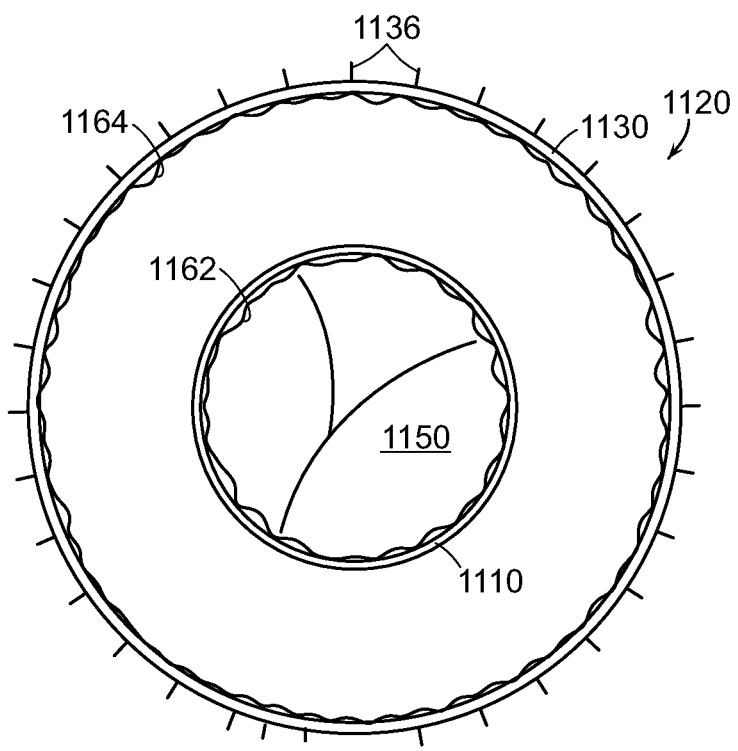

FIG. 12A is a side cross-sectional view and FIG. 12B is a top plan view of a prosthetic heart valve device ("device") 1100 in accordance with an embodiment of the present technology. The device 1100 includes a valve support 1110, an anchoring member 1120 attached to the valve support 1110, and a prosthetic valve assembly 1150 within the valve support 1110. Referring to FIG. 12A, the valve support 1110 has an inflow region 1112 and an outflow region 1114. The prosthetic valve assembly 1150 is arranged within the valve support 1110 to allow blood to flow from the inflow region 1112 through the outflow region 1114 (arrows BF), but prevent blood from flowing in a direction from the outflow region 1114 through the inflow region 1112.

In the embodiment shown in FIG. 12A, the anchoring member 1120 includes a base 1122 attached to the outflow region 1114 of the valve support 1110 and a plurality of arms 1124 projecting laterally outward from the base 1122. The anchoring member 1120 also includes a fixation structure 1130 extending from the arms 1124. The fixation structure 1130 can include a first portion 1132 and a second portion 1134. The first portion 1132 of the fixation structure 1130, for example, can be an upstream region of the fixation structure 1130 that, in a deployed configuration as shown in FIG. 12A, is spaced laterally outward apart from the inflow region 1112 of the valve support 1110 by a gap G. The second portion 1134 of the fixation structure 1130 can be a downstream-most portion of the fixation structure 1130. The fixation structure 1130 can be a cylindrical ring (e.g., straight cylinder or conical), and the outer surface of the fixation structure 1130 can define an annular engagement surface configured to press outwardly against a native annulus of a heart valve (e.g., a mitral valve). The fixation structure 1130 can further include a plurality of fixation elements 1136 that project radially outward and are inclined toward an upstream direction. The fixation elements 1136, for example, can be barbs, hooks, or other elements that are inclined only in the upstream direction (e.g., a direction extending away from the downstream portion of the device 1100).

Referring still to FIG. 12A, the anchoring member 1120 has a smooth bend 1140 between the arms 1124 and the fixation structure 1130. For example, the second portion 1134 of the fixation structure 1130 extends from the arms 1124 at the smooth bend 1140. The arms 1124 and the fixation structure 1130 can be formed integrally from a continuous strut or support element such that the smooth bend 1140 is a bent portion of the continuous strut. In other embodiments, the smooth bend 1140 can be a separate component with respect to either the arms 1124 or the fixation structure 1130. For example, the smooth bend 1140 can be attached to the arms 1124 and/or the fixation structure 1130 using a weld, adhesive or other technique that forms a smooth connection. The smooth bend 1140 is configured such that the device 1100 can be recaptured in a capsule or other container after the device 1100 has been at least partially deployed.

The device 1100 can further include a first sealing member 1162 on the valve support 1110 and a second sealing member 1164 on the anchoring member 1120. The first and second sealing members 1162, 1164 can be made from a flexible material, such as Dacron® or another type of polymeric material. The first sealing member 1162 can cover the interior and/or exterior surfaces of the valve support 1110. In the embodiment illustrated in FIG. 12A, the first sealing member 1162 is attached to the interior surface of the valve support 1110, and the prosthetic valve assembly 1150 is attached to the first sealing member 1162 and commissure portions of the valve support 1110. The second sealing member 1164 is attached to the inner surface of the anchoring member 1120. As a result, the outer annular engagement surface of the fixation structure 1130 is not covered by the second sealing member 1164 so that the outer annular engagement surface of the fixation structure 1130 directly contacts the tissue of the native annulus.

The device 1100 can further include an extension member 1170. The extension member 1170 can be an extension of the second sealing member 1164, or it can be a separate component attached to the second sealing member 1164 and/or the first portion 1132 of the fixation structure 1130. The extension member 1170 can be a flexible member that, in a deployed state (FIG. 12A), flexes relative to the first portion 1132 of the fixation structure 1130. In operation, the extension member 1170 provides tactile feedback or a visual indicator (e.g., on echocardiographic or fluoroscopic imaging systems) to guide the device 1100 during implantation such that the device 1100 is located at a desired elevation and centered relative to the native annulus. As described below, the extension member 1170 can include a support member, such as a metal wire or other structure, that can be visualized via fluoroscopy or other imaging techniques during implantation. For example, the support member can be a radiopaque wire.

Figure 13A:
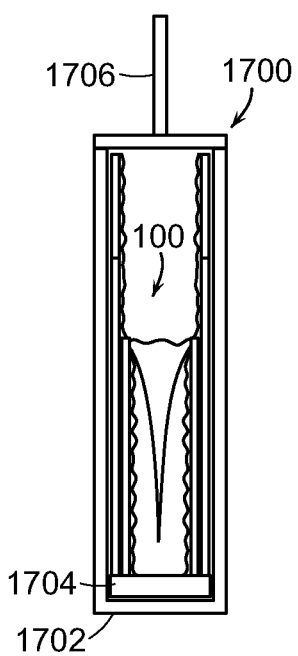
FIGS. 13A and 13B are cross-sectional side views schematically illustrating aspects of delivering a prosthetic heart valve device in accordance with some embodiments of the present technology.
Figure 13B:
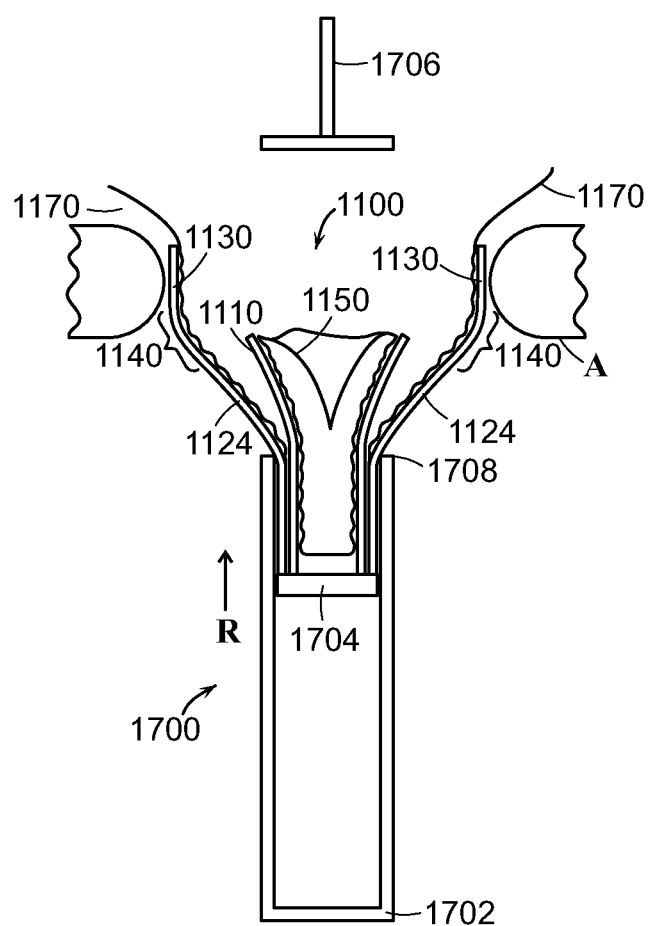

FIGS. 13A and 13B are cross-sectional views illustrating an example of the operation of the smooth bend 1140 between the arms 1124 and the fixation structure 1130 in the recapturing of the device 1100 after partial deployment. FIG. 13A schematically shows the device 1100 loaded into a capsule 1700 of a delivery system in a delivery state, and FIG. 13B schematically shows the device 1100 in a partially deployed state. Referring to FIG. 13A, the capsule 1700 has a housing 1702, a pedestal or support 1704, and a top 1706. In the delivery state shown in FIG. 13A, the device 1100 is in a low-profile configuration suitable for delivery through a catheter or cannula to a target implant site at a native heart valve.

Referring to FIG. 13B, the housing 1702 of the capsule 1700 has been moved distally such that the extension member 1170, fixation structure 1130 and a portion of the arms 1124 have been released from the housing 1702 in a partially deployed state. This is useful for locating the fixation structure 1130 at the proper elevation relative to the native valve annulus A such that the fixation structure 1130 expands radially outward into contact the inner surface of the native annulus A. However, the device 1100 may need to be repositioned and/or removed from the patient after being partially deployed. To do this, the housing 1702 is retracted (arrow R) back toward the fixation structure 1130. As the housing 1702 slides along the arms 1124, the smooth bend 1140 between the arms 1124 and the fixation structure 1130 allows the edge 1708 of the housing 1702 to slide over the smooth bend 1140 and thereby recapture the fixation structure 1130 and the extension member 1170 within the housing 1702. The device 1100 can then be removed from the patient or repositioned for redeployment at a better location relative to the native annulus A. Further aspects of prosthetic heart valve devices in accordance with the present technology and their interaction with corresponding delivery devices are described below with reference to FIGS. 14-25.

Figure 14:
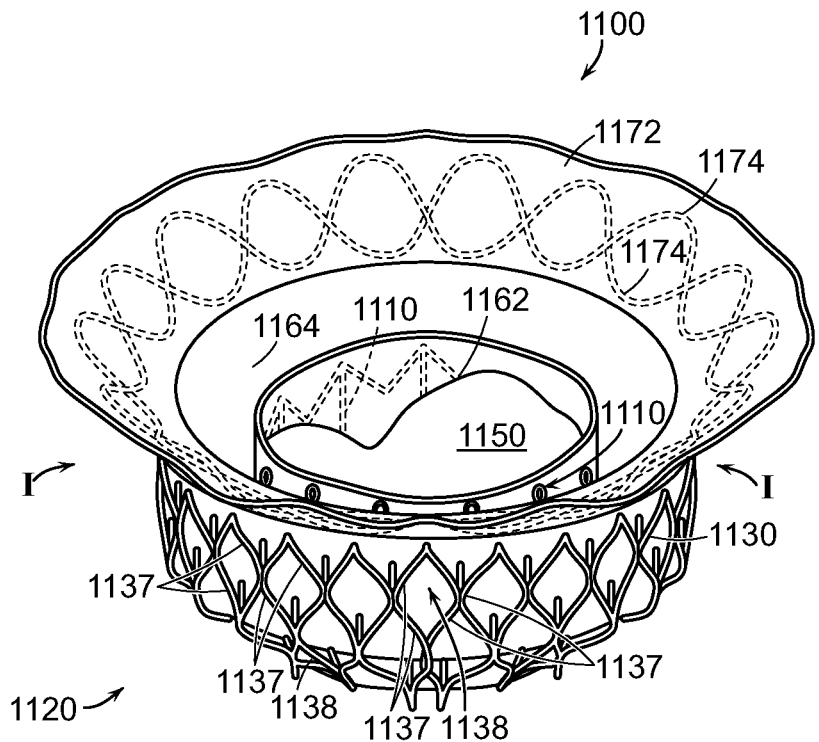
FIG. 14 is a top isometric view of a prosthetic heart valve device in accordance with some embodiments of the present technology.

FIG. 14 is a top isometric view of an example of the device 1100. In this embodiment, the valve support 1110 defines a first frame (e.g., an inner frame) and fixation structure 1130 of the anchoring member 1120 defines a second frame (e.g., an outer frame) that each include a plurality of structural elements. The fixation structure 1130, more specifically, includes structural elements 1137 arranged in diamond-shaped cells 1138 that together form at least a substantially cylindrical ring when freely and fully expanded as shown in FIG. 14. The structural elements 1137 can be struts or other structural features formed from metal, polymers, or other suitable materials that can self-expand or be expanded by a balloon or other type of mechanical expander.

In several embodiments, the fixation structure 1130 can be a generally cylindrical fixation ring having an outwardly facing engagement surface. For example, in the embodiment shown in FIG. 14, the outer surfaces of the structural elements 1137 define an annular engagement surface configured to press outwardly against the native annulus in the deployed state. In a fully expanded state without any restrictions, the walls of the fixation structure 1130 are at least substantially parallel to those of the valve support 1110. However, the fixation structure 1130 can flex inwardly (arrow I) in the deployed state when it presses radially outwardly against the inner surface of the native annulus of a heart valve.

The embodiment of the device 1100 shown in FIG. 14 includes the first sealing member 1162 lining the interior surface of the valve support 1110, and the second sealing member 1164 along the inner surface of the fixation structure 1130. The extension member 1170 has a flexible web 1172 (e.g., a fabric) and a support member 1174 (e.g., metal or polymeric strands) attached to the flexible web 1172. The flexible web 1172 can extend from the second sealing member 1164 without a metal-to-metal connection between the fixation structure 1130 and the support member 1174. For example, the extension member 1170 can be a continuation of the material of the second sealing member 1164. Several embodiments of the extension member 1170 are thus a malleable or floppy structure that can readily flex with respect to the fixation structure 1130. The support member 1174 can have a variety of configurations and be made from a variety of materials, such as a double-serpentine structure made from Nitinol.

Figure 15:
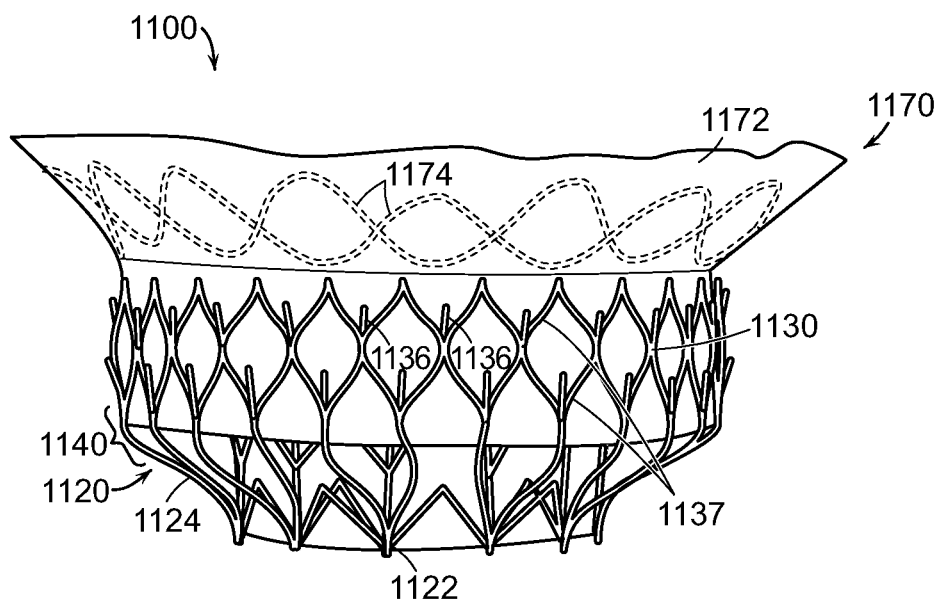
FIG. 15 is a side view and FIG. 16 is a bottom isometric view of the prosthetic heart valve device of FIG. 14.
Figure 16:
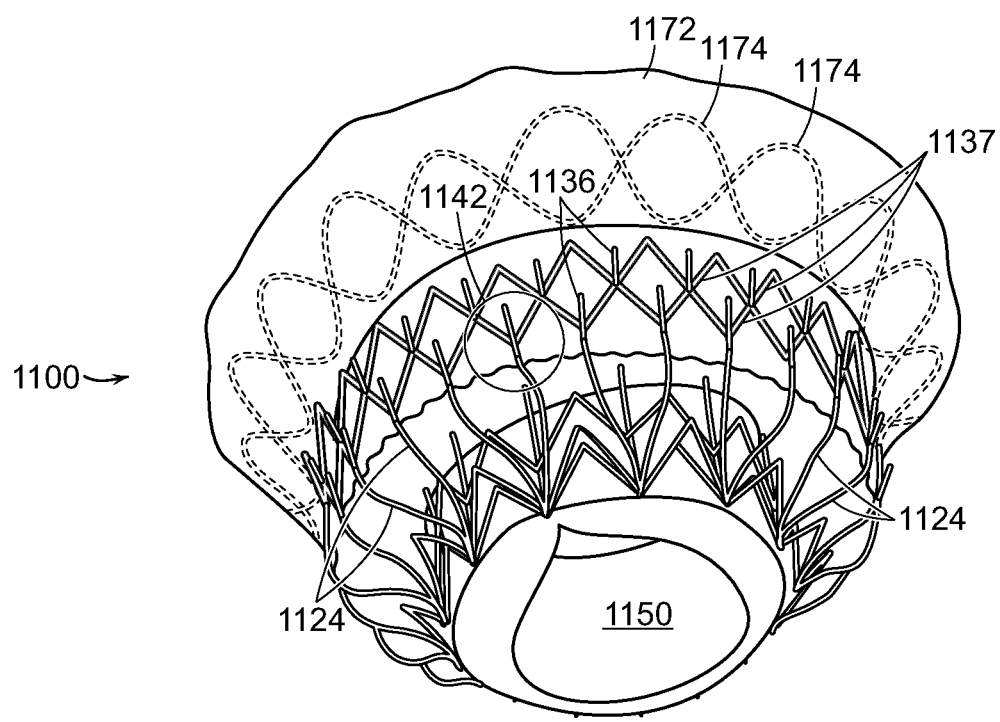

FIG. 15 is a side view and FIG. 16 is a bottom isometric view of the device 1100 shown in FIG. 14. Referring to FIG. 15, the arms 1124 extend radially outward from the base portion 1122 at an angle α selected to position the fixation structure 1130 radially outward from the valve support 1110 (FIG. 14) by a desired distance in a deployed state. The angle α is also selected to allow the edge 1708 of the delivery system housing 1702 (FIG. 13B) to slide from the base portion 1122 toward the fixation structure 1130 during recapture. In many embodiments, the angle α is 15°-75°, or more specifically 15°-60°, or still more specifically 30°-45°. The arms 1124 and the structural elements 1137 of the fixation structure 1130 can be formed from the same struts (i.e., formed integrally with each other) such that the smooth bend 1140 is a continuous, smooth transition from the arms 1124 to the structural elements 1137. This is expected to enable the edge 1708 of the housing 1702 to more readily slide over the smooth bend 1140 in a manner that allows the fixation structure 1130 to be recaptured in the housing 1702 of the capsule 1700 (FIG. 13B). Additionally, by integrally forming the arms 1124 and the structural elements 1137 with each other, it inhibits damage to the device 1100 at a junction between the arms 1124 and the structural elements 1137 compared to a configuration in which the arms 1124 and structural elements 1137 are separate components and welded or otherwise fastened to each other.

Referring to FIGS. 15 and 16, the arms 1124 are also separated from each other along their entire length from where they are connected to the base portion 1122 through the smooth bend 1140 (FIG. 15) to the structural elements 1137 of the fixation structure 1130. The individual arms 1124 are thus able to readily flex as the edge 1708 of the housing 1702 (FIG. 13B) slides along the arms 1124 during recapture. This is expected to reduce the likelihood that the edge 1708 of the housing 1702 will catch on the arms 1124 and prevent the device 1100 from being recaptured in the housing 1702.

In one embodiment, the arms 1124 have a first length from the base 1122 to the smooth bend 1140, and the structural elements 1137 of the fixation structure 1130 at each side of a cell 1138 (FIG. 14) have a second length that is less than the first length of the arms 1124. The fixation structure 1130 is accordingly less flexible than the arms 1124. As a result, the fixation structure 1130 is able to press outwardly against the native annulus with sufficient force to secure the device 1100 to the native annulus, while the arms 1124 are sufficiently flexible to fold inwardly when the device is recaptured in a delivery device.

In the embodiment illustrated in FIGS. 14-16, the arms 1124 and the structural elements 1137 are configured such that each arm 1124 and the two structural elements 1137 extending from each arm 1124 formed a Y-shaped portion 1142 (FIG. 16) of the anchoring member 1120. Additionally, the right-hand structural element 1137 of each Y-shaped portion 1142 is coupled directly to a left-hand structural element 1137 of an immediately adjacent Y-shaped portion 1142. The Y-shaped portions 1142 and the smooth bends 1140 are expected to further enhance the ability to slide the housing 1702 along the arms 1124 and the fixation structure 1130 during recapture.

Figure 17:
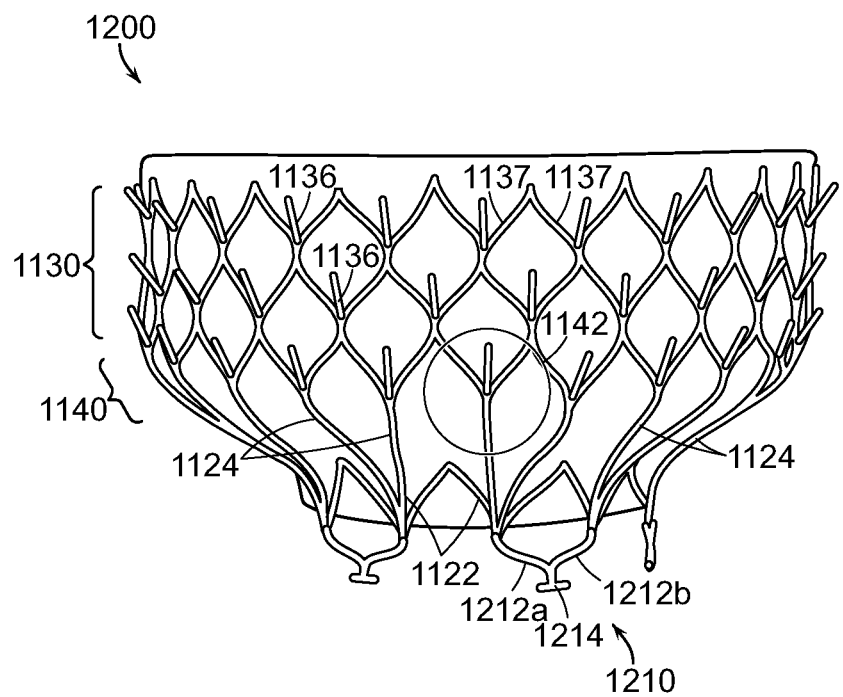
FIG. 17 is a side view and FIG. 18 is a bottom isometric view of a prosthetic heart valve device in accordance with some embodiments of the present technology.
Figure 18:
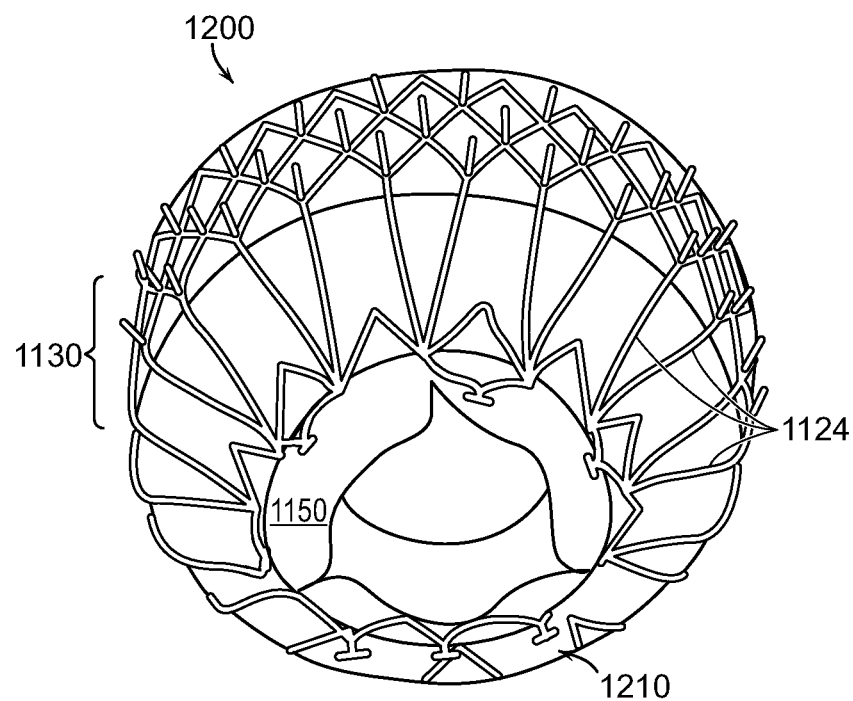

FIG. 17 is a side view and FIG. 18 is a bottom isometric view of a prosthetic heart valve device ("device") 1200 in accordance with another embodiment of the present technology. The device 1200 is shown without the extension member 1170 (FIGS. 14-16), but the device 1200 can further include the extension member 1170 described above. The device 1200 further includes extended connectors 1210 projecting from the base 1122 of the anchoring member 1120. Alternatively, the extended connectors 1210 can extend from the valve support 1110 (FIGS. 12A-16) in addition to or in lieu of extending from the base 1122 of the anchoring member 1120. The extended connectors 1210 can include a first strut 1212a attached to one portion of the base 1122 and a second strut 1212b attached to another portion of the base 1122. The first and second struts 1212a-b are configured to form a V-shaped structure in which they extend toward each other in a downstream direction and are connected to each other at the bottom of the V-shaped structure. The V-shaped structure of the first and second struts 1212a-b causes the extension connector 1210 to elongate when the device 1200 is in a low-profile configuration within the capsule 1700 (FIG. 13A) during delivery or partial deployment. When the device 1200 is fully released from the capsule 1700 (FIG. 13A) the extension connectors 1210 foreshorten to avoid interfering with blood flow along the left ventricular outflow tract.

The extended connectors 1210 further include an attachment element 1214 configured to releasably engage a delivery device. The attachment element 1214 can be a T-bar or other element that prevents the device 1200 from being released from the capsule 1700 (FIG. 13A) of a delivery device until desired. For example, a T-bar type attachment element 1214 can prevent the device 1200 from moving axially during deployment or partial deployment until the housing 1702 (FIG. 13A) moves beyond the portion of the delivery device engaged with the attachment elements 1214. This causes the attachment elements 1214 to disengage from the capsule 1700 (FIG. 13A) as the outflow region of the valve support 1110 and the base 1122 of the anchoring member 1120 fully expand to allow for full deployment of the device 1200.

Figure 19:
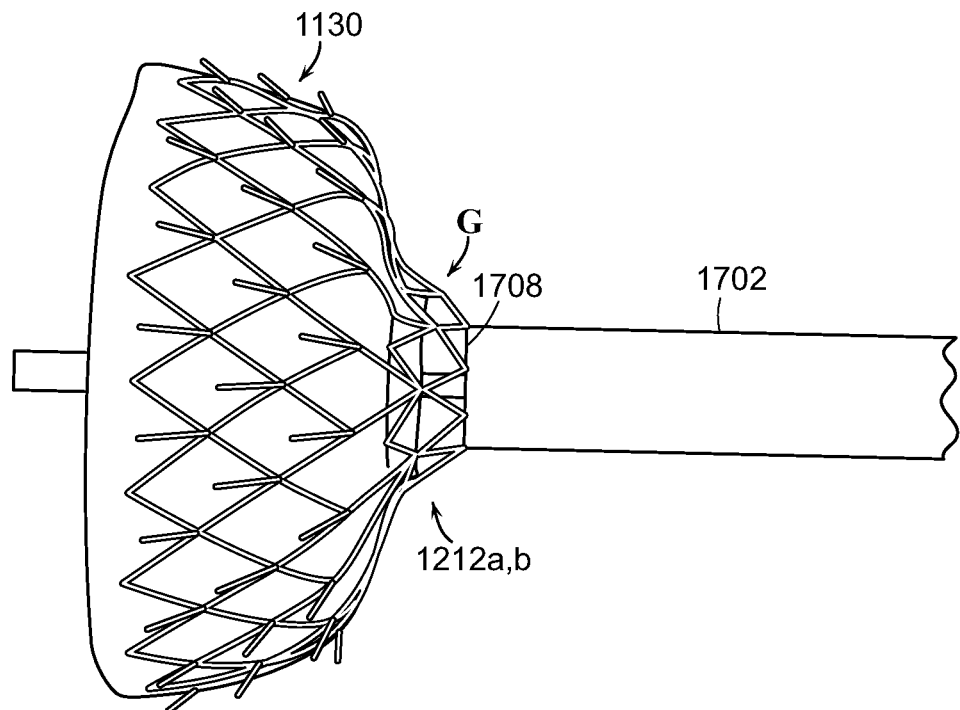
FIG. 19 is a side view and FIG. 20 is a bottom isometric view of the prosthetic heart valve device of FIGS. 17 and 18 at a partially deployed state with respect to a delivery device.
Figure 20:
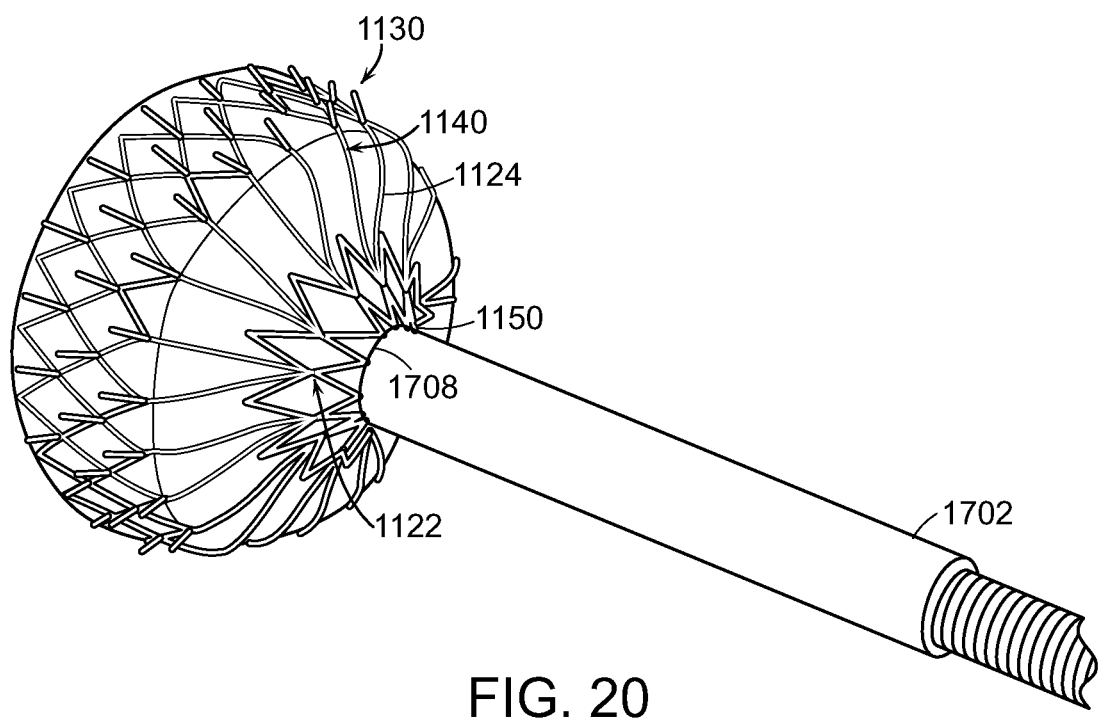

FIG. 19 is a side view and FIG. 20 is a bottom isometric view of the device 1200 in a partially deployed state in which the device 1200 is still capable of being recaptured in the housing 1702 of the delivery device 1700. Referring to FIG. 19, the device 1200 is partially deployed with the fixation structure 1130 substantially expanded but the attachment elements 1214 (FIG. 17) still retained within the capsule 1700. This is useful for determining the accuracy of the position of the device 1200 and allowing blood to flow through the functioning replacement valve during implantation while retaining the ability to recapture the device 1200 in case it needs to be repositioned or removed from the patient. In this state of partial deployment, the elongated first and second struts 1212a-b of the extended connectors 1210 space the base 1122 of the anchoring member 1120 and the outflow region of the valve support 1110 (FIG. 12A) apart from the edge 1708 of the capsule 1700 by a gap G.

Referring to FIG. 20, the gap G enables blood to flow through the prosthetic valve assembly 1150 while the device 1200 is only partially deployed. As a result, the device 1200 can be partially deployed to determine (a) whether the device 1200 is positioned correctly with respect to the native heart valve anatomy and (b) whether proper blood flow passes through the prosthetic valve assembly 1150 while the device 1200 is still retained by the delivery system 1700. As such, the device 1200 can be recaptured if it is not in the desired location and/or if the prosthetic valve is not functioning properly. This additional functionality is expected to significantly enhance the ability to properly position the device 1200 and assess, in vivo, whether the device 1200 will operate as intended, while retaining the ability to reposition the device 1200 for redeployment or remove the device 1200 from the patient.

Figure 21:
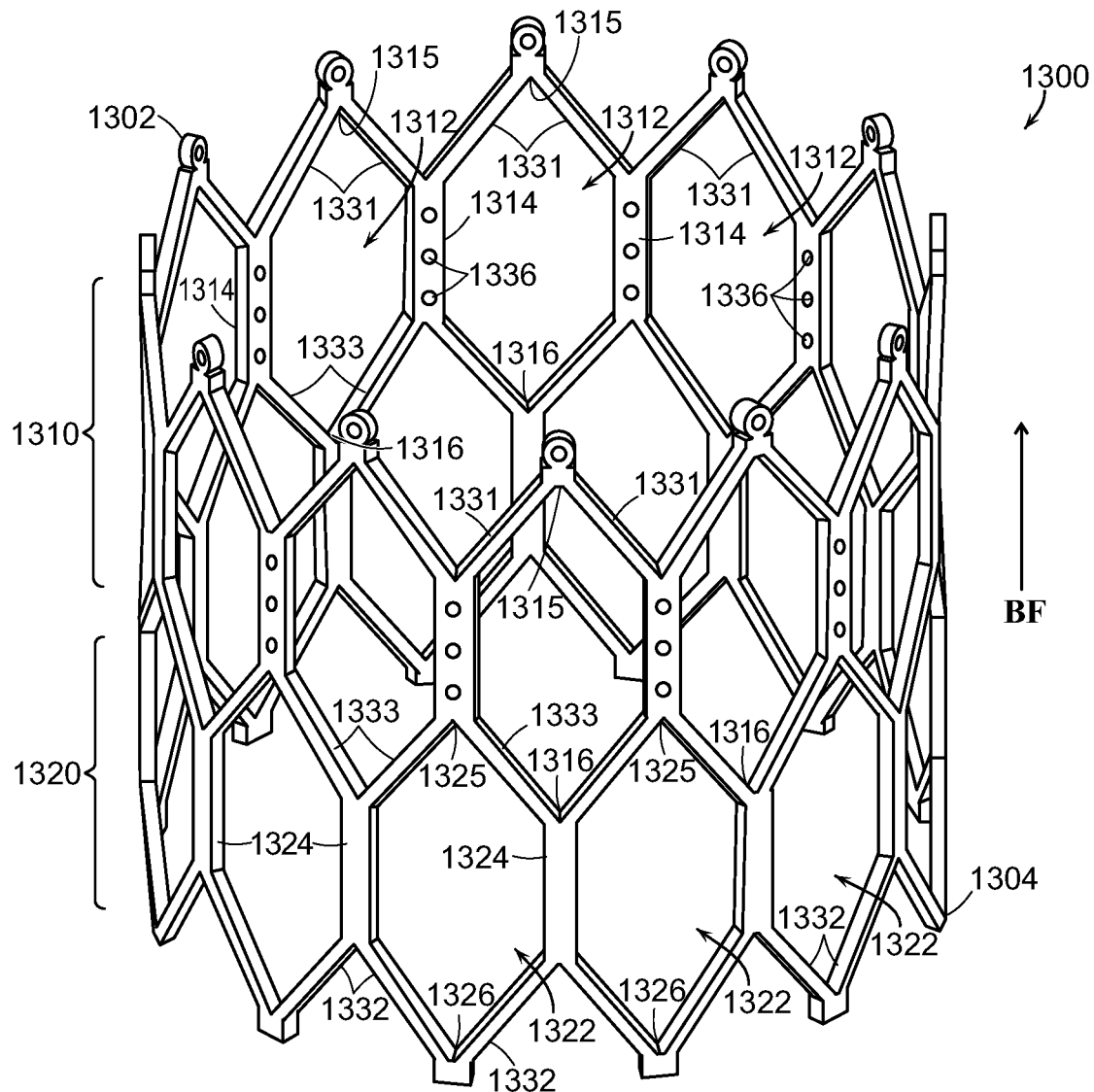
FIG. 21 is an isometric view of a valve support for use with prosthetic heart valve devices in accordance with the present technology.

FIG. 21 is an isometric view of a valve support 1300 in accordance with an embodiment of the present technology. The valve support 1300 can be an embodiment of the valve support 1110 described above with respect to FIGS. 12A-20. The valve support 1300 has an outflow region 1302, an inflow region 1304, a first row 1310 of first hexagonal cells 1312 at the outflow region 1302, and a second row 1320 of second hexagonal cells 1322 at the inflow region 1304. For purposes of illustration, the valve support shown in FIG. 21 is inverted compared to the valve support 1110 shown in FIGS. 12A-20 such that the blood flows through the valve support 1300 in the direction of arrow BF. In mitral valve applications, the valve support 1300 would be positioned within the anchoring member 1120 (FIG. 12A) such that the inflow region 1304 would correspond to orientation of the inflow region 1112 in FIG. 12A and the outflow region 1302 would correspond to the orientation of the outflow region 1114 in FIG. 12A.

Each of the first hexagonal cells 1312 includes a pair of first longitudinal supports 1314, a downstream apex 1315, and an upstream apex 1316. Each of the second hexagonal cells 1322 can include a pair of second longitudinal supports 1324, a downstream apex 1325, and an upstream apex 1326. The first and second rows 1310 and 1312 of the first and second hexagonal cells 1312 and 1322 are directly adjacent to each other. In the illustrated embodiment, the first longitudinal supports 1314 extend directly from the downstream apexes 1325 of the second hexagonal cells 1322, and the second longitudinal supports 1324 extend directly from the upstream apexes 1316 of the first hexagonal cells 1312. As a result, the first hexagonal cells 1312 are offset from the second hexagonal cells 1322 around the circumference of the valve support 1300 by half of the cell width.

In the embodiment illustrated in FIG. 21, the valve support 1300 includes a plurality of first struts 1331 at the outflow region 1302, a plurality of second struts 1332 at the inflow region 1304, and a plurality of third struts 1333 between the first and second struts 1331 and 1332. Each of the first struts 1331 extends from a downstream end of the first longitudinal supports 1314, and pairs of the first struts 1331 are connected together to form first downstream V-struts defining the downstream apexes 1315 of the first hexagonal cells 1312. In a related sense, each of the second struts 1332 extends from an upstream end of the second longitudinal supports 1324, and pairs of the second struts 1332 are connected together to form second upstream V-struts defining the upstream apexes 1326 of the second hexagonal cells 1322. Each of the third struts 1333 has a downstream end connected to an upstream end of the first longitudinal supports 1314, and each of the third struts 1333 has an upstream end connected to a downstream end of one of the second longitudinal supports 1324. The downstream ends of the third struts 1333 accordingly define a second downstream V-strut arrangement that forms the downstream apexes 1325 of the second hexagonal cells 1322, and the upstream ends of the third struts 1333 define a first upstream V-strut arrangement that forms the upstream apexes 1316 of the first hexagonal cells 1312. The third struts 1333, therefore, define both the first upstream V-struts of the first hexagonal cells 1312 and the second downstream V-struts of the second hexagonal cells 1322.

The first longitudinal supports 1314 can include a plurality of holes 1336 through which sutures can pass to attach a prosthetic valve assembly and/or a sealing member. In the embodiment illustrated in FIG. 21, only the first longitudinal supports 1314 have holes 1336. However, in other embodiments the second longitudinal supports 1324 can also include holes either in addition to or in lieu of the holes 1336 in the first longitudinal supports 1314.

Figure 23:
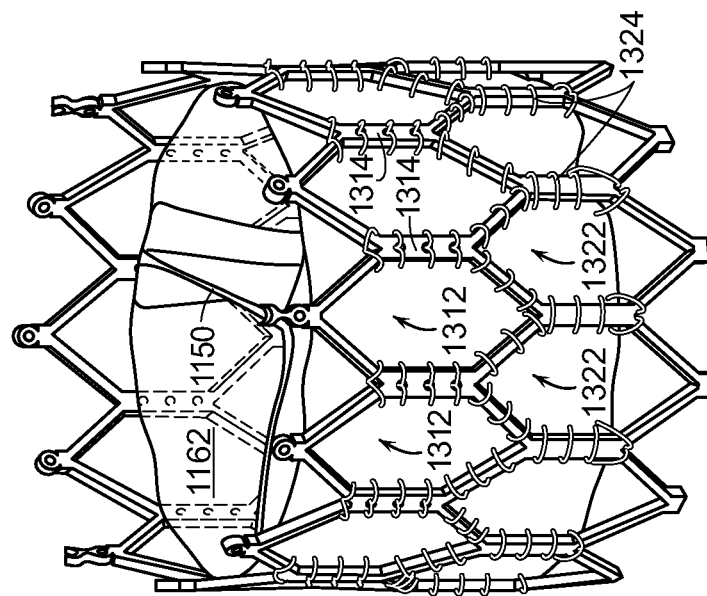
FIGS. 22 and 23 are side and bottom isometric views, respectively, of a prosthetic heart valve attached to the valve support of FIG. 21.
Figure 22:
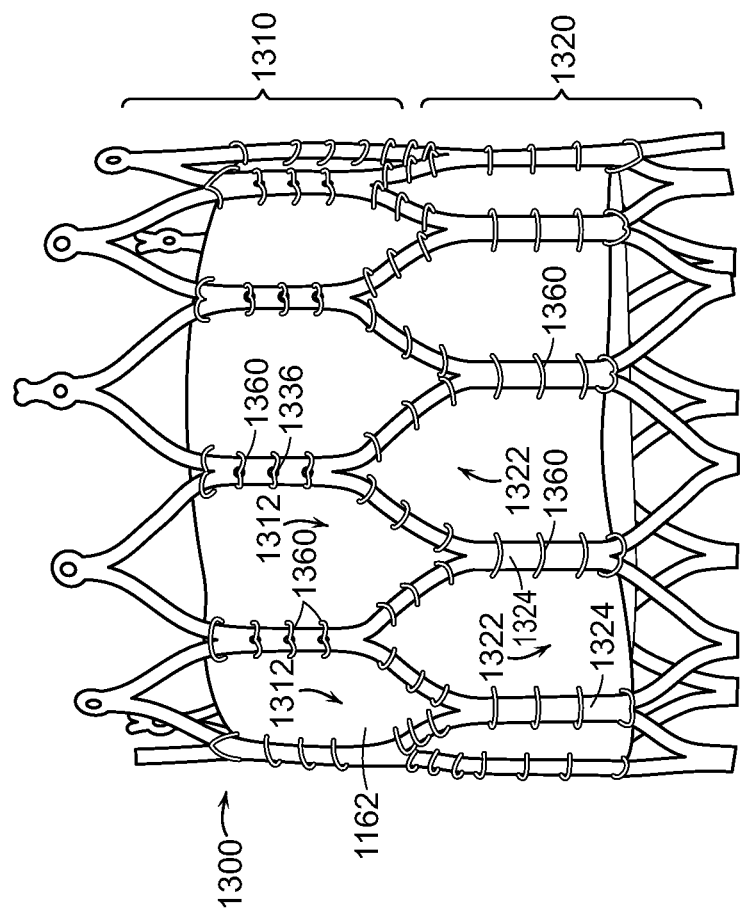

FIG. 22 is a side view and FIG. 23 is a bottom isometric view of the valve support 1300 with a first sealing member 1162 attached to the valve support 1300 and a prosthetic valve 1150 within the valve support 1300. The first sealing member 1162 can be attached to the valve support 1300 by a plurality of sutures 1360 coupled to the first longitudinal supports 1314 and the second longitudinal supports 1324. At least some of the sutures 1360 coupled to the first longitudinal supports 1314 pass through the holes 1336 to further secure the first sealing member 1162 to the valve support 1300.

Referring to FIG. 23, the prosthetic valve 1150 can be attached to the first sealing member 1162 and/or the first longitudinal supports 1314 of the valve support 1300. For example, the commissure portions of the prosthetic valve 1150 can be aligned with the first longitudinal supports 1314, and the sutures 1360 can pass through both the commissure portions of the prosthetic valve 1150 and the first sealing member 1162 where the commissure portions of the prosthetic valve 1150 are aligned with a first longitudinal support 1314. The inflow portion of the prosthetic valve 1150 can be sewn to the first sealing member 1162.

The valve support 1300 illustrated in FIGS. 21-23 is expected to be well suited for use with the device 1200 described above with reference to FIGS. 17-20. More specifically, the first struts 1331 cooperate with the extended connectors 1210 (FIGS. 17-20) of the device 1200 to separate the outflow portion of the prosthetic valve 1150 from the capsule 1700 (FIGS. 19-20) when the device 1200 is in a partially deployed state. The first struts 1331, for example, elongate when the valve support 1300 is not fully expanded (e.g., at least partially contained within the capsule 1700) and foreshorten when the valve support is fully expanded. This allows the outflow portion of the prosthetic valve 1150 to be spaced further apart from the capsule 1700 in a partially deployed state so that the prosthetic valve 1150 can at least partially function when the device 1200 (FIGS. 17-20) is in the partially deployed state. Therefore, the valve support 1300 is expected to enhance the ability to assess whether the prosthetic valve 1150 is fully operational in a partially deployed state.

Figure 24:
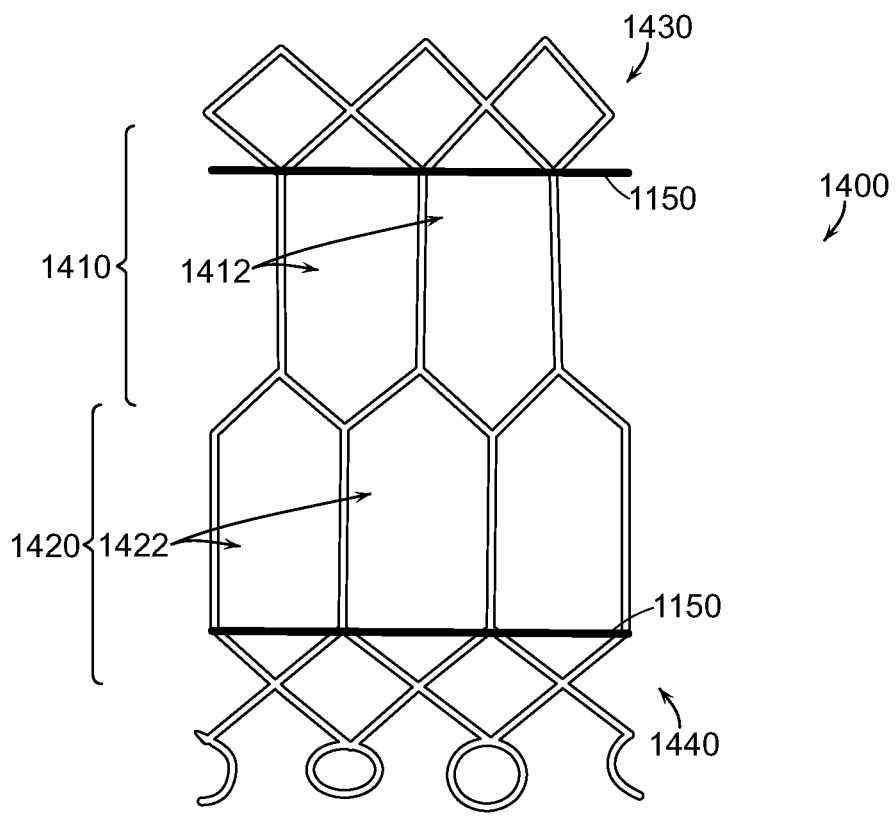
FIGS. 24 and 25 are side views schematically showing valve supports in accordance with additional embodiments of the present technology.
Figure 25:
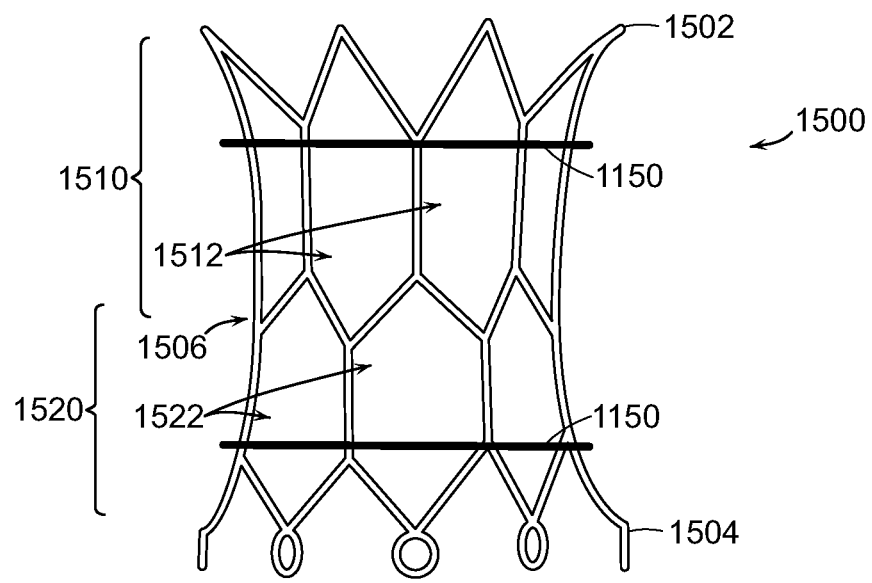

FIGS. 24 and 25 are schematic side views of valve supports 1400 and 1500, respectively, in accordance with other embodiments of the present technology. Referring to FIG. 24, the valve support 1400 includes a first row 1410 of first of hexagonal cells 1412 and a second row 1420 of second hexagonal cells 1422. The valve 1400 can further include a first row 1430 of diamond-shaped cells extending from the first hexagonal cells 1412 and a second row 1440 of diamond-shaped cells extending from the second hexagonal cells 1422. The additional diamond-shaped cells elongate in the low-profile state, and thus they can further space the prosthetic valve 1150 (shown schematically) apart from a capsule of a delivery device. Referring to FIG. 25, the valve support 1500 includes a first row 1510 of first hexagonal cells 1512 at an outflow region 1502 and a second row 1520 of second hexagonal cells 1522 at an inflow region 1504. The valve support 1500 is shaped such that an intermediate region 1506 (between the inflow and outflow regions 1502 and 1504) has a smaller cross-sectional area than that of the outflow region 1502 and/or the inflow region 1504. As such, the first row 1510 of first hexagonal cells 1512 flares outwardly in the downstream direction and the second row 1520 of second hexagonal cells 1522 flares outwardly in the upstream direction.

Examples

Several aspects of the present technology are set forth in the following examples.

1. A system for delivering a prosthetic heart valve device into a heart of a patient, the system comprising:
   an elongated catheter body;
   a delivery capsule carried by the elongated catheter body, the delivery capsule including a platform and a housing having a sidewall and a proximal rim, the housing being configured to slide along the platform from a containment configuration to a deployment configuration, and the platform and the sidewall defining a chamber for retaining a prosthetic heart valve device in the containment configuration; and
   an expandable atraumatic member associated with the capsule, the atraumatic member having an opening, an atraumatic surface, and a peripheral portion, wherein the atraumatic member is configured to be in (a) a compacted configuration in which the atraumatic member is within the chamber in the containment configuration and (b) an expanded configuration in which the peripheral portion extends laterally outward over the proximal rim of the housing in the deployment configuration.

2. The system of example 1 wherein the housing is open at the proximal rim such that the chamber is open facing proximally in the containment configuration.

3. The system of any of the foregoing examples wherein the atraumatic member comprises a truncated conical member.

4. The system of any of the foregoing examples wherein the truncated conical member comprises foam, an elastomer, or a braided wire.

5. The system of any of the foregoing examples wherein the atraumatic member comprises a hub and arms that flare outwardly in the expanded configuration.

6. The system of example 5 wherein the arms comprise a shape memory material.

7. The system of any of the foregoing examples wherein the atraumatic member comprises arms having distal portions that flare radially outward in a distal direction in the expanded configuration.

8. The system of any of the foregoing examples wherein the atraumatic surface is an inclined surface that flares outwardly in a distal direction.

9. The system of example 8 wherein the inclined surface is defined by an outwardly flared arm.

10. The system of any of the foregoing examples, further comprising a prosthetic heart valve device in a low-profile state in the chamber in the containment configuration, and wherein the atraumatic member is within a distal portion of the prosthetic heart valve device in the compacted configuration.

11. A system for treating a native heart valve, comprising:
   an elongated catheter body;
   a delivery capsule carried by the elongated catheter body, the delivery capsule including a support and a housing, the support having a platform, the housing having a sidewall and a proximal rim, and the housing being configured to slide along the platform from a containment configuration to a deployment configuration, and wherein the housing and the platform define a chamber in the containment configuration;
   an expandable prosthetic heart valve device at least partially within the chamber of the housing in the containment configuration; and an expandable atraumatic member carried by the capsule, the atraumatic member having an opening through which the support extends, a proximal atraumatic surface, and a peripheral portion, wherein the atraumatic member is configured to (a) have a first diameter in a compacted configuration and (b) expand outwardly to a second diameter greater than the first diameter in an expanded configuration when the prosthetic heart valve device is released from the chamber such that the peripheral portion extends laterally outward of the proximal rim of the housing.

12. The system of example 11 wherein, when the atraumatic member is in the compacted configuration, the atraumatic member is between the support of the capsule and the prosthetic heart valve device.

13. The system of any of examples 11-12 wherein the atraumatic member comprises a truncated conical member.

14. The system of example 13 wherein the truncated conical member comprises foam, an elastomer, or a braided wire.

15. The system of any of examples 11-14 wherein the atraumatic member comprises a hub and arms that flare outwardly in the expanded configuration.

16. The system of example 15 wherein the arms comprise a shape memory material.

17. The system of any of examples 11-16 wherein the atraumatic member comprises a hub and an expandable member attached to the hub, and wherein the expandable member flares radially outward in a distal direction in the expanded configuration.

18. The system of any of examples 11-17 wherein the atraumatic surface is an inclined surface that flares outwardly in a distal direction.

19. The system of example 18 wherein the inclined surface is a foam surface.

20. The system of example 18 wherein the inclined surface is defined by an outwardly flared arm.

21. A method of delivering a prosthetic heart valve device, comprising:
positioning a delivery capsule carrying a prosthetic heart valve at a native heart valve within a heart of a human, wherein the capsule is in a containment configuration;
moving a housing of the capsule from the containment configuration to a deployed configuration whereby the prosthetic heart valve self-expands and releases from the capsule; and
causing an atraumatic member to expand from a compacted configuration in which the atraumatic member has a first diameter to an expanded configuration in which the atraumatic member has a second diameter greater than the first diameter such that a peripheral portion of the atraumatic member extends laterally outward relative to a proximal rim of the housing.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. Additionally, various features of several embodiments of the atraumatic members shown and described with reference to FIGS. 7A-11 can be interchanged with each other. For example, all of the atraumatic member can optionally include a fabric or wire-braided covering. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:
1. A method comprising:
moving a housing of a delivery capsule carrying a prosthetic heart valve from a containment configuration to a deployed configuration while the delivery capsule is positioned at a native heart valve, wherein the movement of the housing is such that the prosthetic heart valve self-expands and releases from the delivery capsule, wherein the delivery capsule is carried by a distal portion of an elongated body;
expanding an expandable atraumatic member from a compacted configuration in which the atraumatic member has a first diameter to an expanded configuration in which the expandable atraumatic member has a second diameter greater than the first diameter such that a peripheral portion of the atraumatic member extends laterally outward relative to a proximal rim of the housing, wherein with the expandable atraumatic member in the expanded configuration and the housing in the deployed configuration, the expandable atraumatic member is disposed adjacent the proximal rim of the housing; and
withdrawing the delivery capsule and the expandable atraumatic member in a proximal direction relative to the prosthetic heart valve with the expandable atraumatic member in the expanded configuration,
wherein the expandable atraumatic member includes an atraumatic surface disposed opposite the proximal rim of the housing with the housing in the deployed configuration and the expandable atraumatic member in the expanded configuration,
wherein the atraumatic surface is an inclined surface that flares outwardly in a distal direction.

2. The method of claim 1, further comprising, prior to moving the housing, positioning the delivery capsule carrying the prosthetic heart valve at the native heart valve while the capsule is in the containment configuration.

3. The method of claim 1, wherein, in the containment configuration, the housing is open at the proximal rim such that the chamber is open facing the proximal direction.

4. The method of claim 1, wherein the atraumatic member comprises a truncated conical member.

5. The method of claim 4, wherein the truncated conical member comprises at least one of a foam, an elastomer, or a braided wire.

6. The method of claim 1, wherein, in the expanded configuration, the atraumatic member comprises a hub and arms that flare outwardly.

7. The method of claim 6, wherein the arms comprise a shape memory material.

8. The method of claim 1, wherein the atraumatic member comprises arms having distal portions that flare radially outward in a distal direction in the expanded configuration.

9. The method of claim 1, wherein the inclined surface is defined by an outwardly flared arm.

10. The method of claim 1, wherein, when the delivery capsule is in the containment configuration, the prosthetic heart valve is in a low-profile state, and wherein, in the compacted configuration, the expandable atraumatic member is disposed within the prosthetic heart valve.

11. The method of claim 1, wherein, when the expandable atraumatic member is in the expanded configuration, at least a portion of the atraumatic surface slopes outwardly in a distal direction to direct the delivery capsule through at least one of an opening or a lumen of a vasculature of a patient when the delivery capsule is withdrawn in a proximal direction from the patient.

12. The method of claim 1, wherein the peripheral portion that is configured to cover the proximal rim of the delivery capsule when the expandable atraumatic member is in the expanded configuration is a distal-most portion of the expandable atraumatic member.

13. The method of claim 1, wherein, when the expandable atraumatic member is in the expanded configuration, the expandable atraumatic member is tapered in a distal direction such that a proximal end of the expandable atraumatic member does not extend laterally outwards over the proximal rim of the housing.

14. A method comprising:

moving a housing of a delivery capsule carrying a prosthetic heart valve from a containment configuration to a deployed configuration while the delivery capsule is positioned at a native heart valve, wherein the movement of the housing is such that the prosthetic heart valve self-expands and releases from the delivery capsule, wherein the delivery capsule is carried by a distal portion of an elongated body;

expanding an expandable atraumatic member from a compacted configuration in which the atraumatic member has a first diameter and is disposed within the capsule and within the prosthetic heart valve to an expanded configuration in which the expandable atraumatic member has a second diameter greater than the first diameter such that a peripheral portion of the atraumatic member extends laterally outward relative to a proximal rim of the housing; and withdrawing the delivery capsule and the expandable atraumatic member in a proximal direction relative to the heart valve prosthesis with the expandable atraumatic member in the expanded configuration.

15. The method of claim 14, further comprising, prior to moving the housing, positioning the delivery capsule carrying the prosthetic heart valve at the native heart valve while the capsule is in the containment configuration.

16. The method of claim 14, wherein the atraumatic member comprises a truncated conical member.

17. The method of claim 14, wherein, in the expanded configuration, the atraumatic member comprises a hub and arms that flare outwardly.

18. The method of claim 14, further comprising withdrawing the delivery capsule proximally from the patient with the expandable atraumatic member in the expanded configuration and an atraumatic surface of the expandable member sloping outwardly in a distal direction.

19. The method of claim 14, wherein the expandable atraumatic member includes an atraumatic surface disposed opposite the proximal rim of the housing with the housing in the deployed configuration and the expandable atraumatic member in the expanded configuration.

* * * * *